United States Patent
Singamaneni et al.

(10) Patent No.: US 10,241,110 B2
(45) Date of Patent: *Mar. 26, 2019

(54) PLASMONIC BIOSENSORS WITH BUILT-IN ARTIFICIAL ANTIBODIES

(71) Applicant: Washington University in St. Louis, St. Louis, MO (US)

(72) Inventors: Srikanth Singamaneni, St. Louis, MO (US); Limei Tian, St. Louis, MO (US); Keng-Ku Liu, Philadelphia, PA (US); Abdennour Abbas, St. Louis, MO (US); Jeremiah J. Morrissey, St. Louis, MO (US); Evan D. Kharasch, St. Louis, MO (US)

(73) Assignee: Washington University in St. Louis, St. Louis, MO (US)

( * ) Notice: Subject to any disclaimer, the term of this patent is extended or adjusted under 35 U.S.C. 154(b) by 262 days.

This patent is subject to a terminal disclaimer.

(21) Appl. No.: 15/030,004

(22) PCT Filed: Oct. 17, 2014

(86) PCT No.: PCT/US2014/061065
§ 371 (c)(1),
(2) Date: Apr. 15, 2016

(87) PCT Pub. No.: WO2015/058046
PCT Pub. Date: Apr. 23, 2015

(65) Prior Publication Data
US 2016/0282341 A1    Sep. 29, 2016

Related U.S. Application Data

(60) Provisional application No. 61/892,320, filed on Oct. 17, 2013.

(51) Int. Cl.
*G01N 33/553* (2006.01)
*G01N 33/543* (2006.01)
*B82Y 15/00* (2011.01)
*G01N 21/65* (2006.01)
*B82Y 40/00* (2011.01)
*B82Y 30/00* (2011.01)

(52) U.S. Cl.
CPC ........ *G01N 33/54373* (2013.01); *B82Y 15/00* (2013.01); *G01N 21/658* (2013.01); *G01N 33/54346* (2013.01); *G01N 33/553* (2013.01); *B82Y 30/00* (2013.01); *B82Y 40/00* (2013.01)

(58) Field of Classification Search
None
See application file for complete search history.

(56) References Cited

U.S. PATENT DOCUMENTS

| | | |
|---|---|---|
| 5,376,556 A | 12/1994 | Tarcha et al. |
| 9,410,949 B2 | 8/2016 | Singamaneni et al. |
| 2012/0184451 A1 | 7/2012 | Singamaneni et al. |

OTHER PUBLICATIONS

Abbas, et al., Hot Spot-Localized Artificial Antibodies for Label-Free Plasmonic Biosensing, Adv Funct Mater., 2013, vol. 23, No. 14, pp. 1789-1797.
Satija, et al., Emerging use of nanostructure films containing capped gold nanoparticles in biosensors, Nanotechnology, Science and Applications, 2010, vol. 3, pp. 171-188.
Stewart, et al., Nanostructured Plasmonic Sensors, Chem. Rev. 2008, vol. 108, pp. 494-521.
Wang, et al., Label-free biosensor based on gold nanoshell monolayers for monitoring biomolecular interactions in diluted whole blood, Biosensors and Bioelectronics, 2008, vol. 23, pp. 1166-1170.
Tian, et al., Gold nanocages with built-in artificial antibodies for label-free plasmonic biosensing, Journal of Materials Chemistry B, 2014, vol. 2, pp. 167-170.

*Primary Examiner* — Christopher L Chin
(74) *Attorney, Agent, or Firm* — Armstrong Teasdale LLP

(57) ABSTRACT

Plasmonic nanotransducers, methods of preparing plasmonic nanotransducers, and methods for label-free detection of target molecules are disclosed. The plasmonic nanotransducers include hollow nanostructure cores and artificial antibodies. The plasmonic nanotransducers are exposed to a biological sample that can contain the specific target molecules. The plasmonic nanotransducers can be analyzed with surface enhanced Raman scattering techniques and/or localized surface plasmon resonance techniques to quantify the amount of the target molecule in the sample.

20 Claims, 29 Drawing Sheets

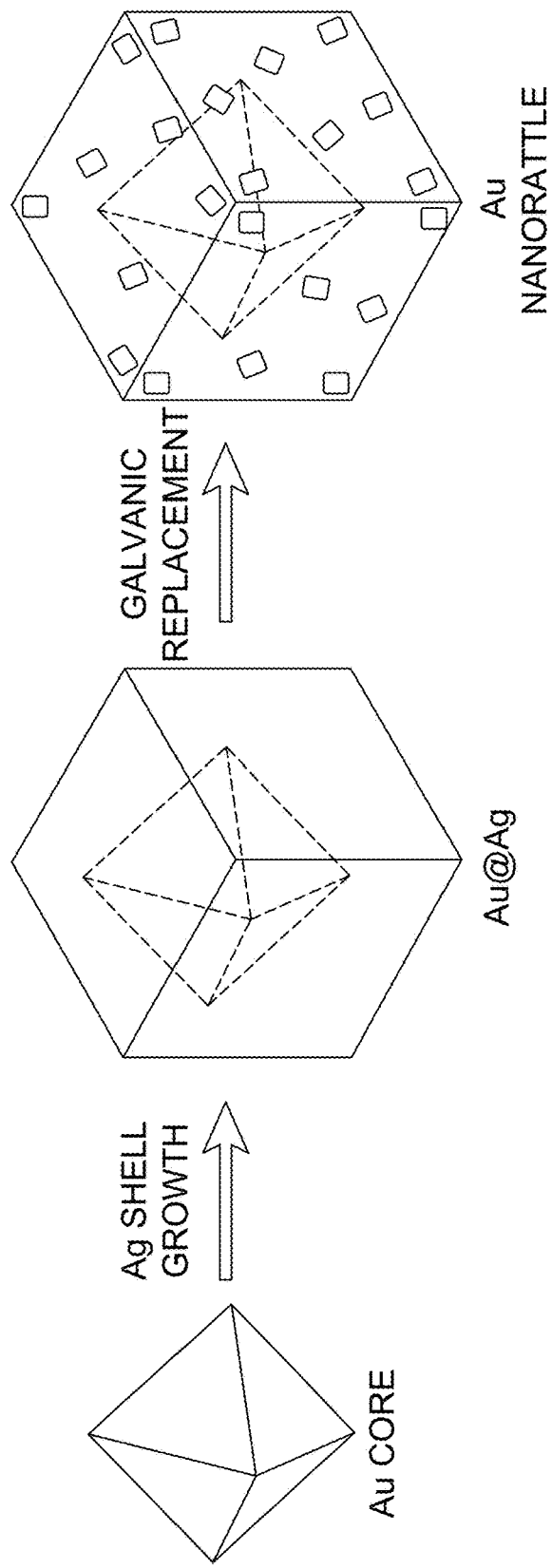

PLASMONIC BIOSENSORS WITH BUILT-IN ARTIFICIAL ANTIBODIES

CROSS REFERENCE TO RELATED APPLICATIONS

This application claims priority to International Application No. PCT/US2014/061065, filed Oct. 17, 2014, which claims priority to U.S. Provisional Patent Application No. 61/892,320, filed Oct. 17, 2013, each of which is hereby incorporated by reference in its entirety.

GOVERNMENT RIGHTS IN THE INVENTION

This invention was made with government support under W81XWH-11-1-0439 awarded by the ARMY/MRMC, CA141521 awarded by the National Institutes of Health, and CBET1254399 awarded by the National Science Foundation. The government has certain rights in the invention.

FIELD OF THE INVENTION

The invention generally relates to systems and methods for detecting biomolecules using plasmonic biosensing. More particularly, the invention relates to systems and methods for detecting biomolecules using molecularly imprinted plasmonic nanotransducers.

BACKGROUND

Biosensing platforms based on localized surface plasmon resonance (LSPR) or surface enhanced Raman scattering (SERS) hold enormous potential to provide highly sensitive, cost-effective, and point-of-care diagnostic tools. However, similar to many other analytical methodologies such as enzyme-linked immunosorbent assays (ELISAs), present plasmonic biosensors use natural antibodies. The use of natural antibodies in analytical methods is ubiquitous, with applications in disease diagnosis, toxicology testing, and biotechnology. Natural antibody production is expensive and time consuming. Both the time and expense required for natural antibody production and their poor stability constitute a barrier to the rapid development and widespread application of plasmonic biosensors and clinical protocols for disease-specific screening.

Although gold nanoparticles may enable LSPR spectroscopy and improve sensitivity, they have so far been used as a layer underneath or on top of a molecularly imprinted polymer (MIP) film. In these configurations, nanoparticles are not used as direct transduction elements but for enhancing Raman scattering from analyte molecules (SERS) or propagating surface plasmon resonance (SPR) on planar gold surfaces. Other reported techniques involve embedding gold nanoparticles in a molecularly imprinted polymer or so-called Au-MIP nanocomposites, which results in a random distribution of the nanoparticles and the molecular imprints. Biomacromolecular imprinting of noble-metal nanoparticles that takes full advantage of the unique structural and localized plasmonic properties of each individual nanoparticle continues to be a serious challenge. Present metal nanostructures have low refractive index sensitivity, which can impede detection of biomolecules at low concentrations.

Most of the existing plasmonic sensors rely on natural antibodies for the capture of target biomolecules (e.g., disease biomarkers). However, natural antibodies suffer from numerous shortcomings such as poor chemical stability, excessive cost and limited shelf-life. Moreover, they pose a significant challenge in efficient integration with abiotic micro- and nanotransduction platforms.

Accordingly, there is a need for structures with a higher refractive index sensitivity for plasmonic biosensing. In addition, there is a need for a sensor with improved chemical stability, increased shelf-life, and more efficient integration with abiotic platforms.

BRIEF DESCRIPTION OF THE DISCLOSURE

The present disclosure is generally directed to systems and methods for detecting biomolecules. More particularly, the invention relates to systems and methods for detecting biomolecules using molecularly imprinted plasmonic nanotransducers.

In one aspect, the present disclosure is directed to a plasmonic nanotransducer comprising a hollow nanostructure core and functional monomers polymerized to the hollow nanostructure core, wherein the polymerized functional monomers comprise at least one recognition cavity that is substantially complementary to a target molecule.

In another aspect, the present disclosure is directed to a method of preparing a plasmonic nanotransducer comprising a hollow nanostructure core and functional monomers adhered to the hollow nanostructure core. The method comprises synthesizing a hollow nanostructure core; immobilizing at least one template molecule on the surface of the hollow nanostructure core to form a template molecule-nanostructure core structure; polymerizing functional monomers onto the template molecule-nanostructure core structure; and removing the template molecule to form at least one recognition cavity in the polymerized functional monomers upon removal of the template molecule, wherein the at least one recognition cavity is substantially complementary to a target molecule.

In another aspect, the present disclosure is directed to a label-free method for detecting a target molecule in a biological sample. The method comprises obtaining a biological sample from the subject; contacting the biological sample with a plasmonic nanotransducer, wherein the plasmonic nanotransducer comprises: a hollow nanostructure core; and functional monomers polymerized to the hollow nanostructure core, wherein the polymerized functional monomers comprise at least one recognition cavity that is substantially complementary to a target molecule; wherein the target molecule in the biological sample forms a complex with the plasmonic nanotransducer; and detecting the complex.

BRIEF DESCRIPTION OF THE DRAWINGS

The following figures illustrate various aspects of the disclosure.

FIG. 15 is a schematic illustrating the synthesis of plasmonic nanorattles.

Corresponding reference characters and labels indicate corresponding elements among the views of the drawings. The headings used in the figures should not be interpreted to limit the scope of the claims.

DETAILED DESCRIPTION

Figure 1A:
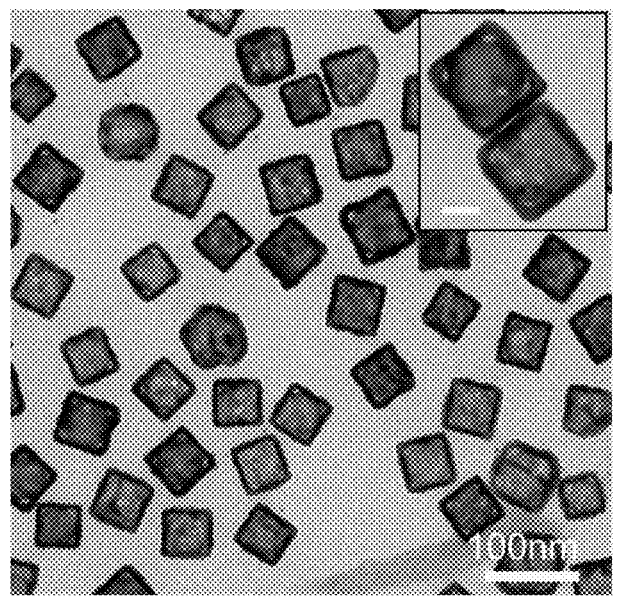
FIG. 1A is a transmission electron micrograph (TEM) image of gold nanocages.

Provided herein are plasmonic nanotransducers, methods for preparing plasmonic nanotransducers, methods for plasmonic biosensing using plasmonic nanotransducers, and methods for preparing plasmonic nanotransducers. The artificial antibodies imprinted on the surface of the nanostructure can include polymerized organo-siloxane monomers. The refractive index sensitivity of localized surface plasmon resonance (LSPR) of plasmonic nanostructures renders them an attractive transduction platform for chemical and biological sensing.

Methods of using the plasmonic nanotransducer for plasmonic biosensing is further provided herein. The method of making a plasmonic nanotransducer can include contacting a nanostructure with a cross linker, contacting the nanostructure with a template biomolecule to create a template on the surface, contacting the template with a plurality of organo-siloxane monomers, and removing the template biomolecule to form a recognition cavity that is substantially complimentary to a target molecule. The recognition cavity that is substantially complimentary to a target molecule results in the artificial antibody capable of capturing the target molecule. The artificial antibody can be formed by the hydrolysis of the organo-siloxane monomers, leaving functional groups to bind to the biomolecule once the template biomolecule is removed.

I. Plasmonic Nanotransducers for Plasmonic Biosensing

In various aspects, plasmonic nanotransducers for plasmonic biosensing include nanostructures with an artificial antibody specific for a target molecule imprinted on the surface of the nanostructure. The artificial antibodies provide for the sensitive and specific detection of target molecules in physiological samples.

The plasmonic nanotransducers include a hollow nanostructure core and functional monomers polymerized to the hollow nanostructure core, wherein the polymerized functional monomers comprise at least one recognition cavity that is substantially complementary to a target molecule.

Suitable hollow nanostructure cores are selected from nanocages, nanorattles, nanoshells, and nanomatryoshkas.

The plasmonic nanotransducers further include functional monomers polymerized to the hollow nanostructure core. Suitable functional monomers can be, for example, silane and acrylamide. Suitable silanes can be, for example, an organic silane monomer, 3-aminopropyltrimethoxysilane, propyltrimethoxysilane, benzyltriethoxysilane, benzyldimethylchlorosilane, acetamidopropyltrimethoxysilane, and combinations thereof.

Organic silane (also referred to herein as "organo-siloxane") monomers can be used to provide amine, hydroxyl and methyl functional groups mimicking a natural antibody and can polymerize around a template biomolecule. In an aspect, the template biomolecule can be recombinant human neutrophil gelatinase-associated lipocalin (NGAL), a biomarker of acute and chronic kidney injury. The template biomolecule can be removed and a target biomolecule within a sample can adsorb or bind to the artificial antibody. In an aspect, the target biomolecule can be NGAL within a patient sample.

Organic silane monomers can further be functionalized with a macromolecule. Suitable macromolecules can be, for example, polyethylene glycol (PEG) and albumin. Suitable albumin can be, for example, bovine serum albumin and human albumin.

In one aspect a macromolecule can be adsorbed to the functional monomers. Suitable macromolecules that can be adsorbed to the functional monomers can be, for example, polyethylene glycol (PEG) and albumin. Suitable albumin can be, for example, bovine serum albumin and human albumin.

A. Hollow Nanostructure Cores

In an aspect, the hollow nanostructure core is selected from nanocages, nanorattles, nanoshells, and nanomatryoshkas.

In an aspect, the hollow nanostructure core of the plasmonic nanotransducer can be a metal hollow nanostructure core. In an aspect, the metal hollow nanostructure core can be a gold nanostructures, silver nanostructures, copper nanostructures, and combinations thereof.

Non-limiting examples of nanostructures for preparing hollow nanostructure cores include nanoparticles, nanocages, nanorods, nanobipyramids, nanostars, nano-octahedra, nanorattles and any other nanostructure capable of molecular imprinting on the surface. In an aspect, the hollow nanostructure core of the plasmonic nanotransducer can be a gold nanocage. In an aspect, the hollow nanostructure core of the plasmonic nanotransducer can be a gold nanorattle. In another aspect, the hollow nanostructure core may be a gold nanorod.

The hollow nanostructure core of the plasmonic nanotransducer includes a metal nanostructure core further including a porous metal shell. Hollow nanostructure cores can be prepared by coating a nanostructure core (e.g., nanoparticles, nanocubes, nanorods, nanobipyramids, nanostars, and nano-octahedra) with a metal to form a metal shell surrounding the nanostructure core. The metal shell can then be treated to form pores in the metal shell, and result in the formation of the hollow nanotransducer. In an exemplary aspect, a gold nanostructure core such as nano-octahedra can be coated with silver to form a bi-metallic core-shell nanostructure having a silver metal shell on the gold nanostructure core. The silver metal shell can then be treated such as using galvanic replacement reaction to convert the silver metal shell into a porous gold shell (see, FIG. 15). The nanostructure core remains embedded in the porous shell. Average pore size in the shell can be about 3 nm. Pore sizes can be determined using transmission electron microscopy.

In an aspect, hollow nanostructure cores such as, for example, nanocages, nanorattles, nanoshells, and nanomatryoshkas, provide a novel class of plasmonic nanostructures that can be used as the nanostructure for the nanotransducer. Nanocages can be about 60 nm per side. AuNCs (gold nanocages) have a highly tunable LSPR into the near infrared (NIR), where the endogenous absorption coefficient of living tissue can be nearly two orders magnitude smaller compared to that in the visible range. In an aspect, nanocages (e.g., gold nanocages) exhibit higher refractive index sensitivity and lower electromagnetic (EM) decay length compared to gold nanorods (AuNRs). Without being limited to a particular theory, the higher refractive index enables lowering the limit of detection (LOD) of the target biomolecules.

B. Molecular Imprinting

Molecular imprinting involves the polymerization of functionalized monomers in the presence of a template molecule (e.g., proteins). The resulting polymerized functional monomers present a complementary conformation to the template molecule and provide chemical interaction with its functional groups. A subsequent release of the template molecule leaves behind a polymeric recognition cavity with the desired shape and chemical functionality that is substantially complementary to the template molecule. The template molecule is selected based on the target molecule to be detected. Because the template molecule shares the same structure as the target molecule, polymeric recognition cavity with the desired shape and chemical functionality that is substantially complementary to the template molecule will also be substantially complementary to the target molecule.

A template molecule is temporarily bound or coupled to the surface of a nanostructure. The template molecule used for molecular imprinting is selected based on the target molecule desired to be detected using the plasmonic nanotransducers. In one aspect, a cross-linker can be used to temporarily bind the template molecule to the surface of the nanostructure. The template molecule can then interact with the functional monomers that are polymerized on the nanostructure and surround the template molecule. Upon removal of the template molecule a recognition cavity is formed by the polymer with the desired shape and chemical functionality that is substantially complementary to the template molecule. Because the template molecule used to form the recognition cavity matches the target molecule desired to be detected, the recognition cavity is also substantially complementary to the target molecule.

Figure 8A:
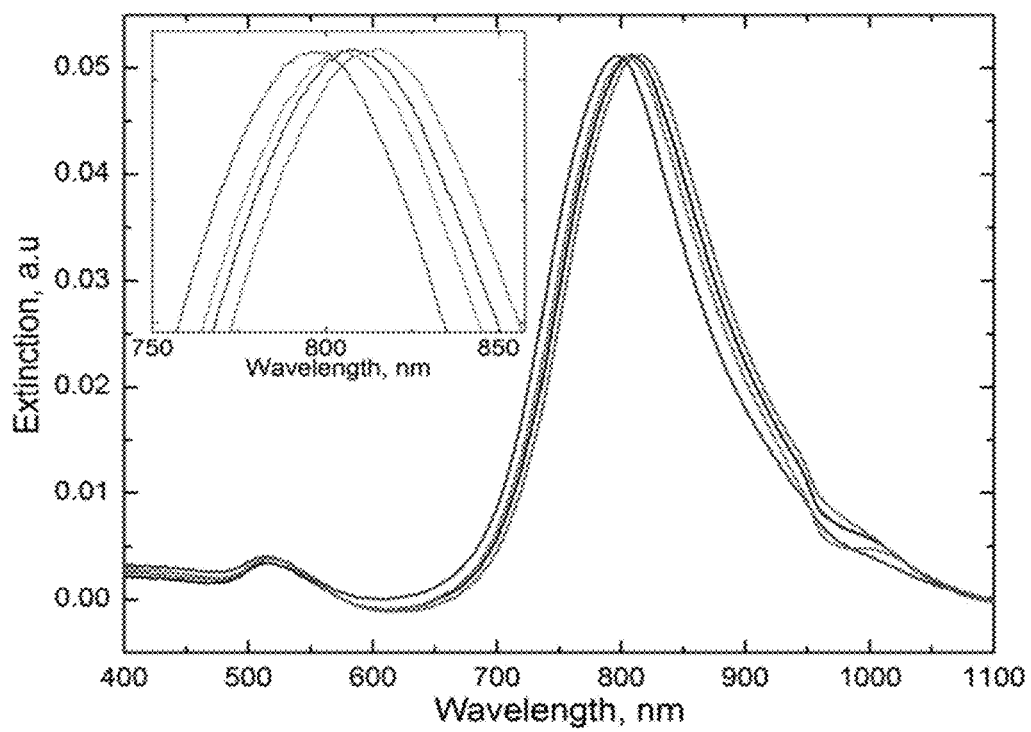
FIG. 8A is a graph summarizing the extinction spectra of gold nanorods at different stages in a molecular imprinting process.
Figure 8B:
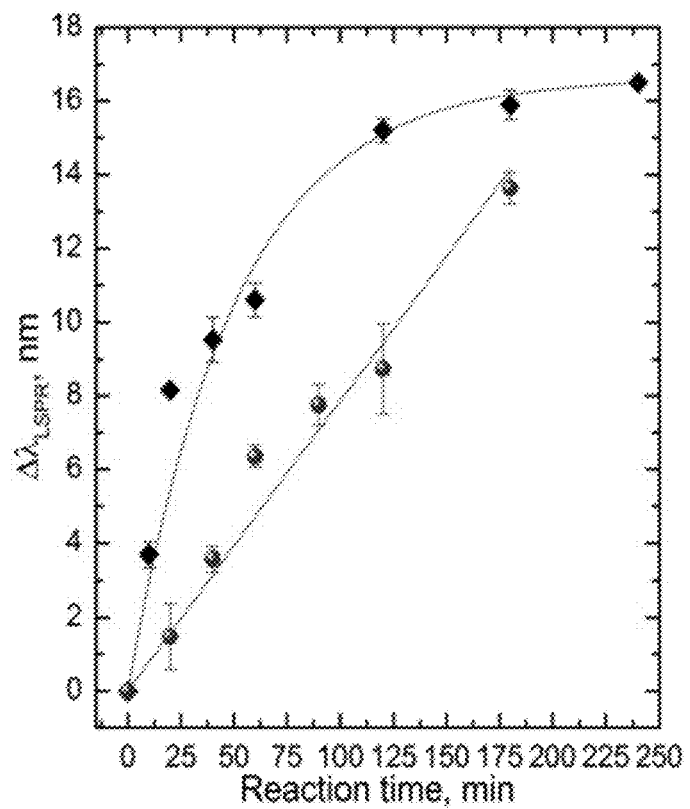
FIG. 8B is a graph summarizing the shift in the LSPR wavelength as a function of the reaction time of p-ATP/GA (squares) and siloxane co-polymerization (circles).

FIG. 8 depicts the structural characterization of the molecular imprinting procedure using a bovine serum albumin (BSA) protein template molecule. FIG. 8A depicts the extinction spectra of the gold nanorods (AuNR) following each step. FIG. 8B is a plot depicting the shift in the LSPR wavelength as a function of the reaction time of p-ATP/GA (black squares) and siloxane co-polymerization (circles). FIG. 8A depicts AFM images after treatment with the cross-linker (p-ATP/GA), immobilization of the protein (BSA) and co-polymerization of the siloxanes (P). The arrows indicate the same nanorods after each step. Higher magnification AFM images are shown in the second row.

The functionalization of the nanostructures by the cross-linker, proteins or the polymerized functional monomers induces a shift in the LSPR wavelength (see e.g., FIG. 8A). Thus, LSPR of nanostructures can be used to monitor the growth of the cross-linker and polymerized functional monomers at the nanoscale level. In an aspect, a 1 nm shift in the LSPR wavelength corresponds to an about 1.2±0.3 nm organic layer thickness for both the cross-linker layer and the polymer layer. FIG. 8B shows the increase in the LSPR wavelength shift as a function of the reaction time of both the mixture p-ATP/GA and the organo-siloxanes monomers. The growth of the cross linker layer could be approximated with an exponential decay fit with a maximum shift of about 16 nm after about 2 h of reaction. This indicates the exponential decay in LSPR sensitivity with increasing distance from the nanostructure surface. On the other hand, the growth of the siloxane copolymer should theoretically follow the same exponential decay behavior. However, the reaction in this case can be much slower and the initial stages of the copolymer growth can be approximated with a linear fit and exhibit a wavelength shift rate of about $\Delta\lambda/t \approx 0.1$ nm/min.

Plasmonic nanotransducers with hollow nanostructure cores and artificial antibodies can be achieved using a molecular imprinting approach. Without being limited to a particular theory, the large refractive index sensitivity and small electromagnetic decay length of plasmonic nanotransducers provide improved nanostructures for plasmonic biosensing. Hollow nanostructures can be surface-imprinted using functional monomers to prepare plasmonic nanotransducers with artificial antibodies (i.e., recognition cavities) as described herein. Polymerization of functional monomers such as silane and acrylamide on hollow nanostructure cores having immobilized template molecules create a molecular imprinted polymer (MIP) film surrounding the hollow nanostructure core and the immobilized template molecules. The fine control of the MIP film thickness as analyzed by LSPR spectroscopy and the non-uniform distribution of the capping ligand around the hollow nanostructure cores can be exploited to favor molecular imprinting in areas that can be potent for plasmonic biosensing. In an aspect, the organo-siloxane monomers, siloxane monomers trimethoxypropylsilane (TMPS) and (3-aminopropyl)trimethoxysilane (APTMS) can be co-polymerized on the hollow nanostructure surface with silane and acrylamide. Use of APTMS and TMPS in aqueous media provides a polymer with amine ($NH_3^+$), hydroxyl (OH) and methyl ($CH_3$) functional groups. Without being limited to a particular theory, concerted weak interactions such as, electrostatic, hydrogen bonding and hydrophobic interactions, are believed to be the form of interaction in recognition cavity-target molecule complexes. The composition ratio of the co-polymerization can be adjusted to result in flexibility and mechanical strength of the polymer.

In addition to monitoring the imprinting process, LSPR spectroscopy can be used as a detection platform. The capture/release of the target molecule by the artificial antibodies induces a change in the refractive index of the layer surrounding the hollow nanostructure. The recognition and binding of the target molecule can then be detected as a shift in the LSPR wavelength that may be dependent on the concentration of the target molecule.

In an aspect, the plasmonic nanotransducer can be adsorbed to a substrate. The substrate can be a glass substrate, a paper substrate, and a fibrous mat. Suitable paper substrates can be, for example, cellulose paper, nitrocellulose paper, methylcellulose paper, hydroxypropylcellulose paper, and nanocellulose paper. Suitable fibrous mats can be, for example, a woven fibrous mat and a non-woven fibrous mat.

II. Methods for Preparing Plasmonic Nanotransducers

In an aspect, a method for preparing a plasmonic nanotransducer comprising a hollow nanostructure core and functional monomers adhered to the hollow nanostructure core wherein the polymerized functional monomers comprise at least one recognition cavity that is substantially complimentary to a target molecule is provided. The method includes synthesizing a hollow nanostructure core; immobilizing at least one template molecule on the surface of the hollow nanostructure core to form a template molecule-nanostructure core structure; polymerizing functional monomers onto the template molecule-nanostructure core structure; and removing the template molecule to form at least one recognition cavity in the polymerized functional monomers upon removal of the template molecule, wherein the at least one recognition cavity is substantially complementary to a target molecule.

Suitable nanostructure cores can be, for example, nanocages, nanorattles, nanoshells, and nanomatryoshkas.

Suitable functional monomers are selected from a silane, acrylamide and combinations thereof. Suitable silanes can be selected from an organic silane monomer, 3-aminopropyltrimethoxysilane, propyltrimethoxysilane, benzyltriethoxysilane, benzyldimethylchlorosilane, acetamidopropyltrimethoxysilane, and combinations thereof.

In an aspect, the method can further include adsorbing to the functional monomers a molecule selected from polyethylene glycol and albumin prior to removing the template molecule.

Silane polymerization can be performed by sol-gel methods, where the polysiloxane networks are formed by siloxane bonds between silanol groups. The surface of the silica shells of silica-coated nanostructures can be modified by introducing amine functionality using 3-aminopropyltrimethoxysilane (APTMS). Aldehyde functionality can then be introduced using glutaraldehyde where the amine groups on the silica surface are converted to aldehyde groups. The template molecule can be bound to the surface of the silica-coated nanostructures using the aldehyde groups on the surface of these nanostructures, forming imine bonds. Following immobilization of the template molecule on the surface of the nanostructures, organic silane monomers, APTMS and propyltrimethoxysilane (PTMS) can be polymerized onto the surface at room temperature under buffered conditions to prevent the denaturing of the template molecules.

The template molecule is removed from the template molecule-nanostructure core structure by exposing the template molecule-nanostructure core structure to a reagent selected from an organic acid, an acid reagent, a detergent, and combinations thereof. Suitable reagents can be oxalic acid, sodium dodecyl sulfate (SDS), and combinations thereof. Oxalic acid breaks the imine bond between the silica surface and the template molecule, thus removing the template molecule from the surface. Removal of the template results in recognition cavities within the polymer, which act as specific recognition sites for the rebinding of the template molecule and a target molecule. The possibility of non-specific binding of the molecularly imprinted nanostructures is contemplated. To overcome this issue, polyethylene glycol (PEG) and albumin be used as a passivating layer. In one aspect, the polymer network can be formed using silane monomers functionalized with PEG side chains or albumin. In another aspect, PEG chains or albumin can be grafted to the polymer network before the template molecule is removed.

In an aspect, the method can further include adsorbing to the functional monomer a molecule selected from polyethylene glycol and albumin prior to removing the template molecule. The molecule is adsorbed to the functional monomer prior to removing the template molecule.

In an aspect, the method can further include functionalizing organic silane monomers with a macromolecule selected from polyethylene glycol and albumin. The organic silane monomers are functionalized prior to polymerizing the functional monomers onto the template molecule-nanostructure core structure.

Figure 6:
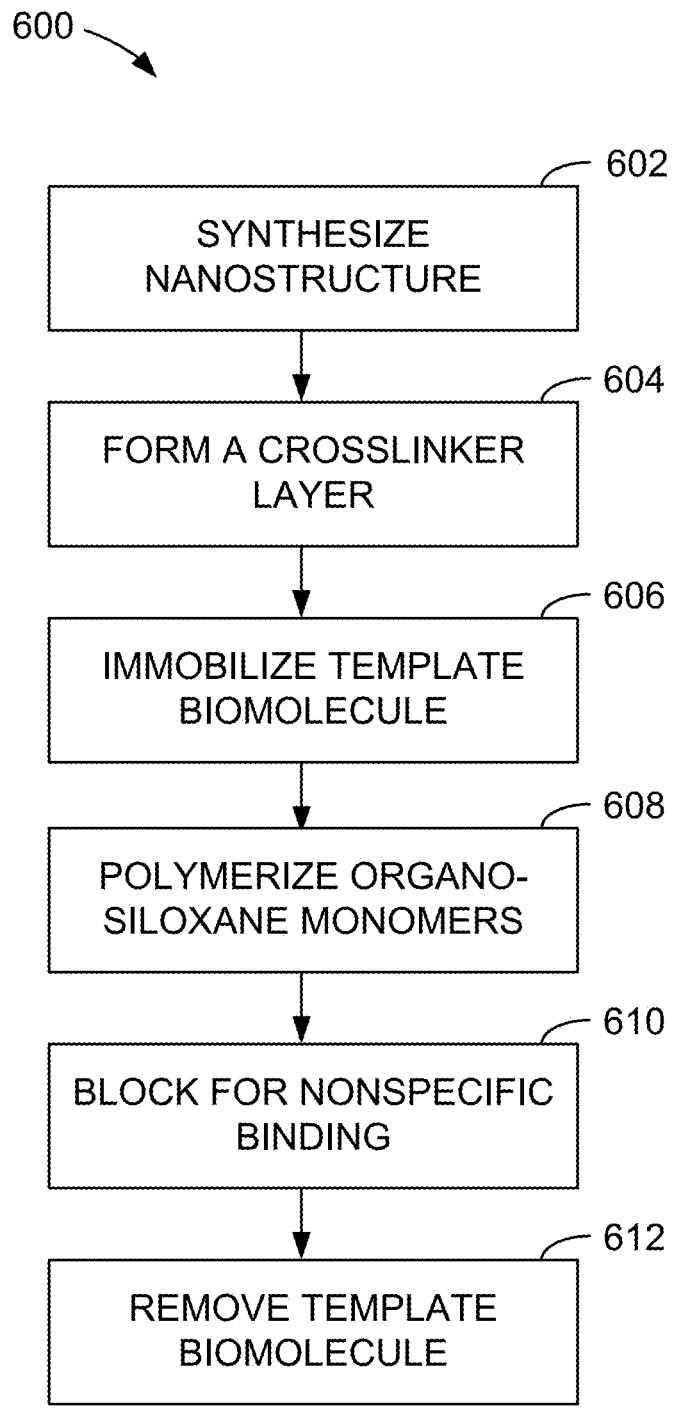
FIG. 6 is a flow chart summarizing the steps of a method for producing a molecularly imprinted nanostructure in an aspect.

FIG. 6 is a block diagram of the method for producing gold nanocage plasmonic biosensors. The method can include synthesizing pristine AuNCs at step 602, forming a cross linker layer at step 604, immobilization of template molecules at step 606, polymerization of organo-siloxane monomers at step 608, and removing the template molecules at step 612. The method can optionally include blocking the AuNCs at step 610 after the polymerization of the organo-siloxane polymers at step 608.

The plasmonic nanotransducers can be adsorbed onto a surface. The surface can be, for example, glass, paper, plastic, or any other surface capable of having nanostructures adsorb to the surface. In an aspect, the surface can be a glass surface.

In an aspect, the cross linker layer can include a p-ATP/GA cross linker layer. The cross linker layer can be used to immobilize the template molecule to the surface of the nanostructure prior to the application of the organo-siloxane monomers.

Organo-siloxane monomers can be polymerized on the surface of the nanostructure and around the template molecule. Without being limited to a particular theory, the organo-siloxane monomers can provide amine, hydroxyl and methyl functional groups mimicking a natural antibody when polymerized around absorbed target molecules. The template molecule and organo-siloxane monomers can mold reversible recognition cavities specific for the template molecule. Polymerization and formation of recognition cavities using the template molecule can be monitored by detecting a shift in LSPR wavelength.

The template molecules can then be removed by breaking imine bonds. In an aspect, the template molecules can be removed using organic acids such as oxalic acid, surfactants such as sodium dodecyl sulfate (SDS), and combinations thereof. Removal of the template molecules forms artificial antibodies (recognition cavities) in the polymer on the surface of the nanostructure.

After the plasmonic nanotransducers are formed, the plasmonic nanotransducers can capture target molecules. The plasmonic nanotransducers can be reusable in an aspect. In this aspect, the captured target molecules can be released from the plasmonic nanotransducers after detection. The captured target molecules can be released by contacting the plasmonic nanotransducers with organic acids such as oxalic acid, surfactants such as sodium dodecyl sulfate (SDS), and combinations thereof. In various aspects, the plasmonic nanotransducer can be reused at least about 5 times. In an aspect, the plasmonic nanotransducers can be reused to recapture target molecules from the same or different sample.

Figure 3:
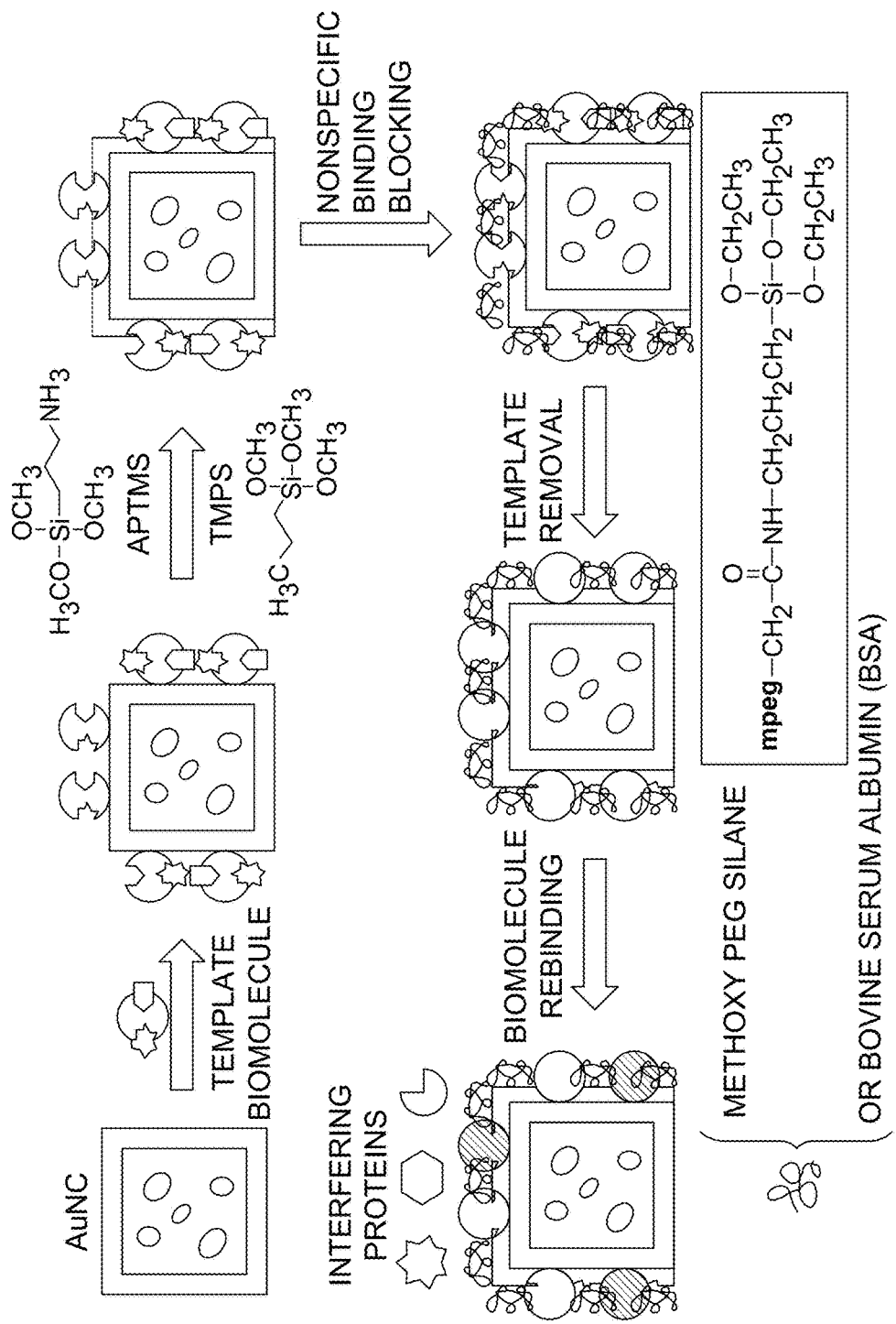
FIG. 3 is a schematic illustration of a process of molecular imprinting on Au nanocages in an aspect.

FIG. 3 is a schematic illustration representing molecular imprinting on Au nanocage plasmonic biosensors and methods for minimizing non-specific binding to artificial antibodies. As shown in FIG. 3, the method can further include preventing non-specific binding of interfering proteins in physiological fluids. These methods involve blocking the siloxane polymer (non-cavity regions) with a synthetic molecule (e.g., silane-terminated polyethylene glycol (Methoxy PEG silane)) or biomacromolecule (e.g., bovine serum albumin (BSA)) before removing the template molecule used to create the recognition cavity. Methoxy PEG silane, a hydrophilic polymer, can provide a flexible and stable protective layer around the artificial antibodies (i.e., reaction cavities in the siloxane copolymer) to reduce nonspecific binding by steric shielding. To prevent non-specific adsorption, BSA can also be employed to modify the surface of siloxane copolymers as blocking agents. BSA has been demonstrated to be an effective blocking agent to prevent non-specific adsorption of proteins in conventional immunoassays using natural antibodies.

III. Label-Free Methods for Plasmonic Biosensing

In another aspect, a label-free method for detecting a target molecule in a biological sample is disclosed. The method includes obtaining a biological sample from the subject; contacting the biological sample with a plasmonic nanotransducer, wherein the plasmonic nanotransducer comprises: a hollow nanostructure core; and functional monomers polymerized to the hollow nanostructure core, wherein the polymerized functional monomers comprise at least one recognition cavity that is substantially complementary to a target molecule; wherein the target molecule in the biological sample forms a complex with the plasmonic nanotransducer; and detecting the complex.

The method can further include detecting the complex using local surface plasmon resonance (LSPR) and surface enhanced Raman scattering (SERS). Surface plasmon involves the collective coherent oscillation of the conductive electrons at the interface of metal and dielectric materials.

Detecting the LSPR wavelength can include directing a light onto the plasmonic nanotransducers and detecting the reflected light using a spectrophotometer. In an aspect, the light can be ambient light. A phase shift in the LSPR wavelength from before contact with the sample and after contact with the sample can indicate binding of the target molecule to the plasmonic nanotransducer.

SERS spectra can be collected using methods known to those skilled in the art. For example, a confocal Raman spectrometer mounted on a Leica microscope equipped with 514.5 and 785 nm lasers and a hand-held spectrometer can be used. For a 785 nm wavelength laser, the focal volume (and spot diameter) of the laser focused with 20× and 50× objectives is 32.3 fl (1.20 µm) and 2.61 fl (0.64 µm), respectively. For moderate detection levels (concentration>1 µg/ml), SERS provides distinct spectral differences due to the strong Raman bands, which are enhanced 105-109 times compared to normal Raman scattering. To achieve the trace level analysis (concentration<100 ng/ml), multivariable statistical means, such as principal component analysis (PCA) via intrinsic Raman spectra of the analyte of interest, can be employed. Specifically, linear multivariable models of SERS spectra data sets can be built by establishing principal component vectors (PCs), which can provide the statistically most significant variations in the data sets, and reduce the dimensionality of the sample matrix. This approach involves assigning a score for the PCs of each spectrum collected followed by plotting the spectrum as a single data point in a two-dimensional plot. The plot reveals clusters of similar spectra, thus individual biological species (analyte and interfering molecules) can be classified and differentiated.

The limit of detection (LOD) achieved with gold nanocage plasmonic nanotransducers can be more than an order of magnitude lower compared to that obtained with gold nanorods. Additionally, the LOD achieved with gold nanocage plasmonic nanotransducers can be employed for rapid analysis of a physiological (biological) sample.

The hollow nanostructure core of the plasmonic transducers can be any of those described herein. Particularly suitable hollow nanostructure cores can be nanocages and nanorattles. Suitable hollow nanostructure cores can be gold nanostructure cores, a silver nanostructure cores, a copper nanostructure cores, and combinations thereof.

The biological sample can be a liquid biological sample. In an aspect, the liquid biological sample is selected from the group consisting of whole blood, plasma, serum, urine, saliva, cerebrospinal fluid, and sweat. In an aspect, the liquid biological sample can be a cell extract such as a cell homogenate.

The target molecule is selected from the group consisting of a cell, a protein, a peptide, a nucleic acid, and combinations thereof.

Plasmonic nanotransducers exhibit stability across a pH ranging from about 4.5 to about 8.5. In various aspects, the plasmonic nanotransducers exhibit stability across pH ranges from about 4.5 to about 5.5, from about 5 to about 6, from about 5.5 to about 6.5, from about 6 to about 7, from about 6.5 to about 7.5, from about 7 to about 8, and about 7.5 to about 8.5. Plasmonic nanotransducers can produce a stable LSPR signal over a specific gravity ranging from about 1.005 to about 1.030.

In an aspect, plasmonic nanotransducers enable the detection of protein biomarkers. As described herein, template molecules used for molecular imprinting are selected based on the protein biomarker to be detected as the target molecule. In an aspect, plasmonic nanotransducers can exhibit improved selectivity against numerous interfering urinary proteins and stability across pH ranging from 4.5 to 8.5 and specific gravities from 1.005 to 1.030. The urinary protein biomarker, neutrophil gelatinase-associated lipocalin (NGAL) can be detected in urine for kidney injury. Other urinary proteins such as adipophilin (ADFP) and aquaporin-1 (AQP1) provide excellent candidates for the noninvasive and early detection of renal cancer carcinoma (RCC).

The plasmonic nanotransducer can be employed in point-of-care setting to rapidly screen patients for specific biomolecules. In an aspect, plasmonic nanotransducer with artificial antibodies can be used to screen patients for biomarkers known to be associated with diseases to enable early therapeutic intervention.

EXAMPLES

The following examples are included to demonstrate preferred embodiments of the invention. It should be appreciated by those of skill in the art that the techniques disclosed in the examples that follow represent techniques discovered by the inventors to function in the practice of the invention, and thus can be considered to constitute preferred modes for its practice. However, those of skill in the art should, in light of the present disclosure, appreciate that changes can be made in the specific embodiments which are disclosed and obtain a like or similar result without departing from the scope of the invention.

Example 1: Nanorod Synthesis and Deposition

AuNRs were synthesized using a seed-mediated approach. Seed solution was prepared by adding 1 ml of an ice-cold solution of 10 mM sodium borohydride to 10 ml of 0.1M cetyltrimethylammonium bromide (CTAB) and 2.5× $10^{-4}$M HAuC$_{14}$ (aq.) solution under magnetic stirring at room temperature. The color of the solution changed from yellow to brown. Growth solution was prepared by mixing 95 ml of 0.1M CTAB, 1 ml of 10 mM silver nitrate, 5 ml of 10 mM HAuC$_{14}$, and 0.55 ml of 0.1M ascorbic acid in the same order. The solution was homogenized by gentle stirring. To the resulting colorless solution, 0.12 ml of freshly prepared seed solution was added and set aside in the dark for 14 h. The solution turned from colorless to violet brown with most of the color change happening in the first hour. Prior to use, AuNR solution was centrifuged twice at 13,000 rpm for 10 min to remove excess CTAB and then redispersed in nanopure water. The synthesized nanorods had an average size 20 nm×60 nm.

Cetyltrimethyl-ammonium bromide (CTAB)-capped AuNRs with an aspect ratio ranging from 2 to 3.5 were synthesized using a seed-mediated approach. The nanorods were then adsorbed onto poly(2-vinyl pyridine)-modified glass substrate). Nanorod-coated glass and silica substrates were prepared by first exposing the piranha-cleaned glass surface to 4% poly(2-vinylpyridine) (P2VP) solution in ethanol for 1 h, followed by rinsing with ethanol. The modified glass substrates were then exposed to nanorod solution overnight. Finally the substrates were thoroughly rinsed with water to remove the weakly adsorbed nanorods and then dried with nitrogen flux.

Example 2: Macromolecular Imprinting Procedure

The molecularly imprinted AuNRs were prepared in three steps: first, the nanorod-coated glass substrate were immersed in a freshly prepared 2 mL phosphate buffer saline solution (PBS, pH8.3) containing 20 µL of glutaraldehyde (25%) and 20 µL of pATP (4 mM in ethanol). The immersion time determines the thickness of the cross linker film (p-ATP/GA). An immersion time of 10 min provided an LSPR shift of 2-3 nm, corresponding to about 3 nm thickness. The substrates were then rinsed gently with buffer and kept in the same buffer solution.

Figure 8C:
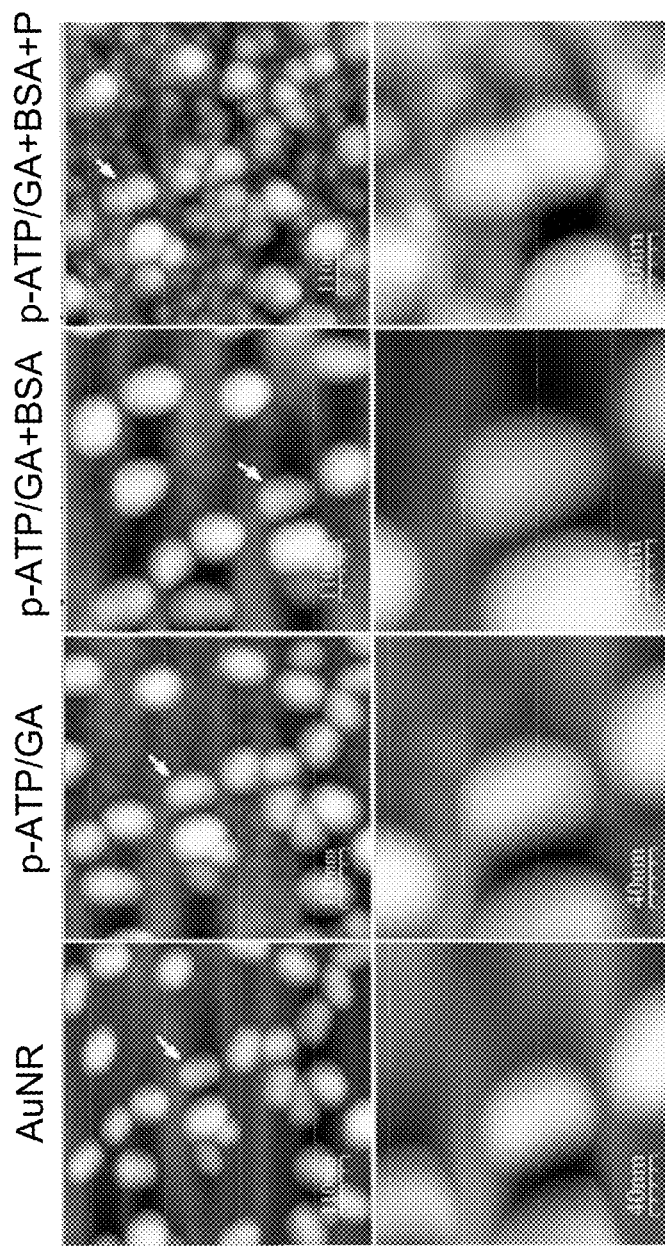
FIG. 8C is a series of AFM images after treatment with the cross-linker (p-ATP/GA), immobilization of the protein (BSA) and co-polymerization of the siloxanes (P).

To evaluate the actual film thickness corresponding to the LSPR shift rate, AFM imaging of the same nanorods was performed following each step of the imprinting process. As shown in FIG. 8C, the size of the nanorods increased after each step and the thickness measurement indicated that a 1 nm shift in the LSPR wavelength corresponded to 1.2±0.3 nm organic layer thickness for both the cross linker film and siloxane co-polymer. Based on these results, a p-ATP/GA treatment for 10 min followed by 40 min polymerization of the siloxane monomers lead to a thickness increase of about 3.5 nm for each step, thus keeping the protein template molecules at less than 5 nm distance from the nanorods surface while resulting in a partial coverage of the protein template molecules with the siloxane copolymers.

The immobilization of the protein templates was achieved by exposing the AuNRs to a mixture of p-aminothiophenol (p-ATP) and glutaraldehyde (GA) (p-ATP/GA). In aqueous solutions, p-ATP binds spontaneously to gold surfaces with its thiol group, while GA molecules form oligomers of variable size with a free aldehyde group at each end of the oligomer molecules. As a result, GA functions as a cross linker between the amine groups of p-ATP molecules and the amine moieties on the side chains of the protein template molecules by forming unstable imine bonds in basic pH buffer solution (FIG. 7A).

Figure 7A:
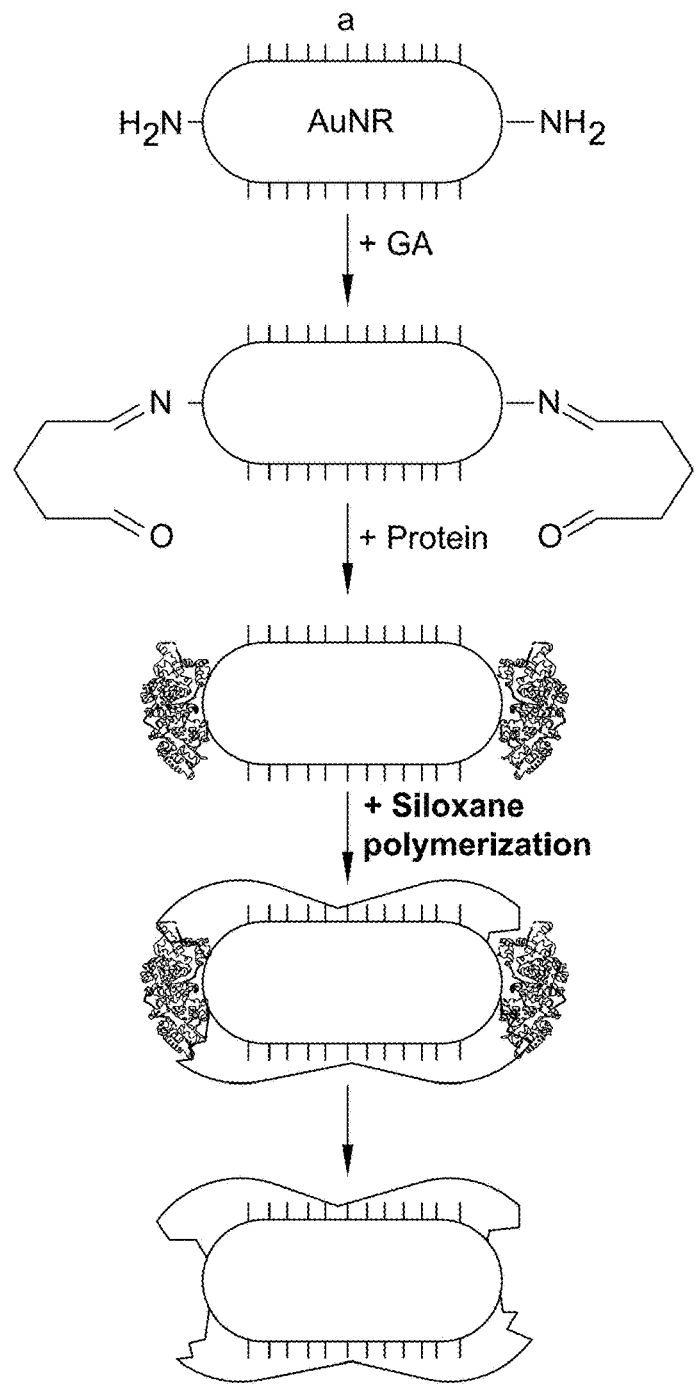
FIG. 7A is a schematic representation of the surface chemistry of a method of molecularly imprinting a gold nanorod in an aspect.
Figure 7B:
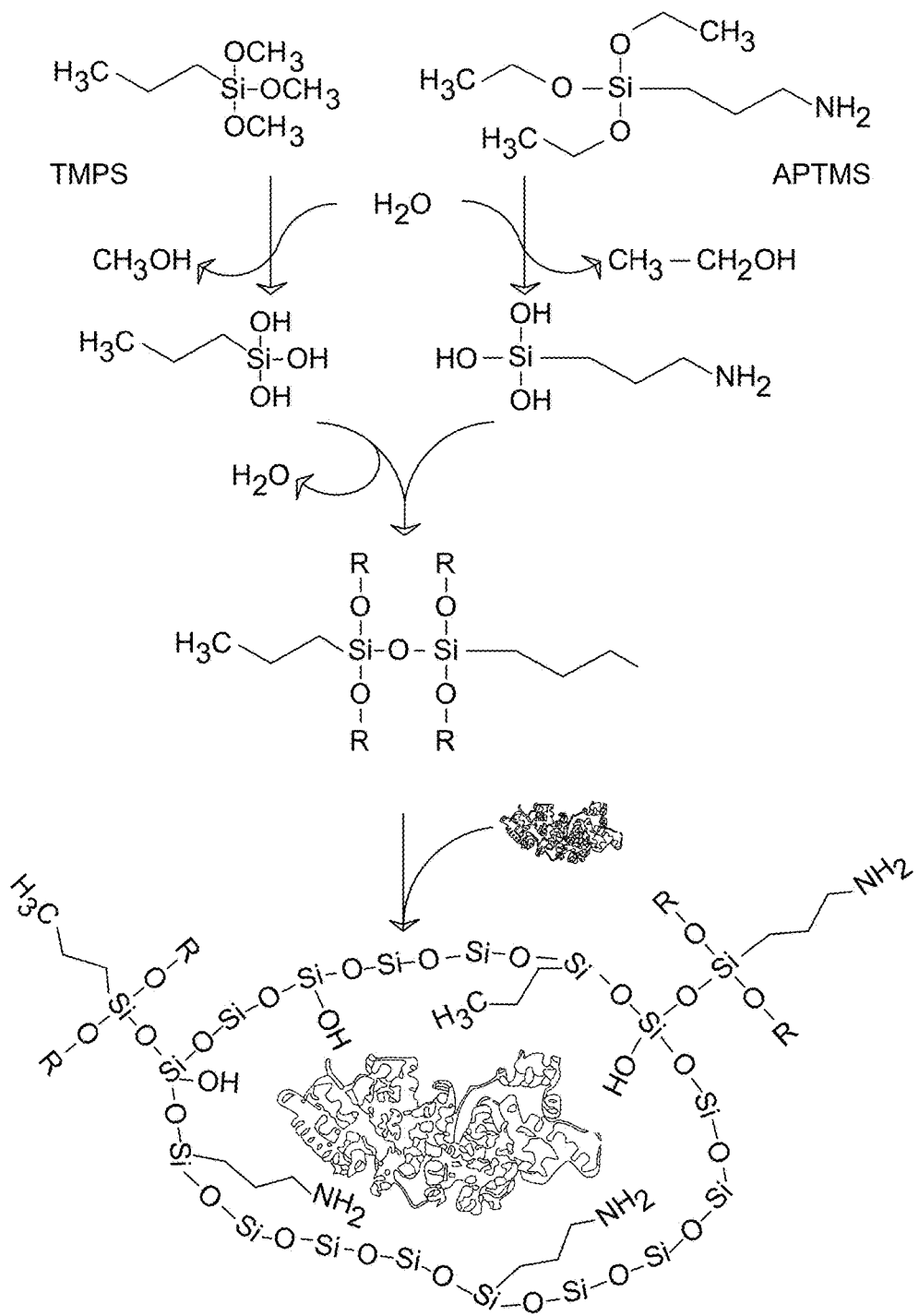
FIG. 7B is a schematic illustration of the co-polymerization reaction of the organo-siloxane monomers APTMS and TMPS.

FIG. 7 depicts the concept and mechanism of plasmonic hot spot-localized imprinting of gold nanorods. FIG. 7A depicts the surface chemistry of the molecular imprinting process involving the preferential attachment of p-ATP to the ends of AuNRs, followed by glutaraldehyde (GA) interaction with the primary amine groups of p-ATP on one side and with the amine functions of the protein template molecules on the other side. Finally, siloxane monomers are polymerized in the presence of the protein template molecules. Removal of the protein template molecule results in a polymeric recognition cavity. FIG. 7B depicts the co-polymerization reaction of the organo-siloxane monomers, APTMS and TMPS. In an aqueous environment, the monomers undergo hydrolysis then condensation to yield amorphous siloxane copolymer.

Protein immobilization was performed by exposing the functionalized substrates to 1 mg/mL bovine serum albumin (BSA; pdb ID: 1E7I, Ip=4.7, MW=66.5 kDa), bovine hemoglobin (Hb; pdb ID: 2HHB, Ip=6.8, MW=64.5 kDa) or 0.5 mg/mL recombinant human neutrophil gelatinase-associated lipocalin (NGAL; pdb ID: 3TZS, Ip=8.9, MW=25 kDa) all prepared in PBS solution (pH 8.3). The exposure was performed under gentle shaking for 30 min followed by 2 h incubation at 4° C.

Following the immobilization of the template, the organo-siloxane monomers trimethoxypropylsilane (TMPS) and (3-aminopropyl)trimethoxysilane (APTMS), which are hydrolytically unstable, were co-polymerized onto the modified AuNR surface. While the Si—C bond and aminopropyl group cannot be cleaved, the ethoxy groups of APTMS and methoxy groups of TMPS undergo rapid hydrolysis to produce ethanol, methanol and trisilanols (FIG. 7B). The subsequent condensation of the transient silanol groups yields an aminopropyl-functional amorphous polymer and entrapment of the protein templates. This sol-gel approach is known to be very versatile and flexible technique, and has been used for molecularly imprinting in a variety of sensors. After rinsing with the same buffer solution, the protein-coated substrates were immersed in 3 mL phosphate buffer (pH 7.5) to which 5 µL TMPS and 5 µL APTMS were freshly added. The immersion time determines the thickness of the polysiloxane co-polymer. An immersion time of 40 min resulted in a polymer thickness of about 5 nm. The samples were then gently rinsed with PBS solution (pH 7.5) and stored in the same buffer overnight at 4° C.

The last step of the molecular imprinting process was the template release by breaking the imine bonds of the cross linker using a mixture of sodium dodecyl sulfate and oxalic acid. The protein template molecules inside the siloxane co-polymer were extracted by exposing the imprinted substrates to a mixture of 2% SDS and 2 mM oxalic acid for 1 h.

Example 3: Characterization During Molecular Imprinting

Figure 9A:
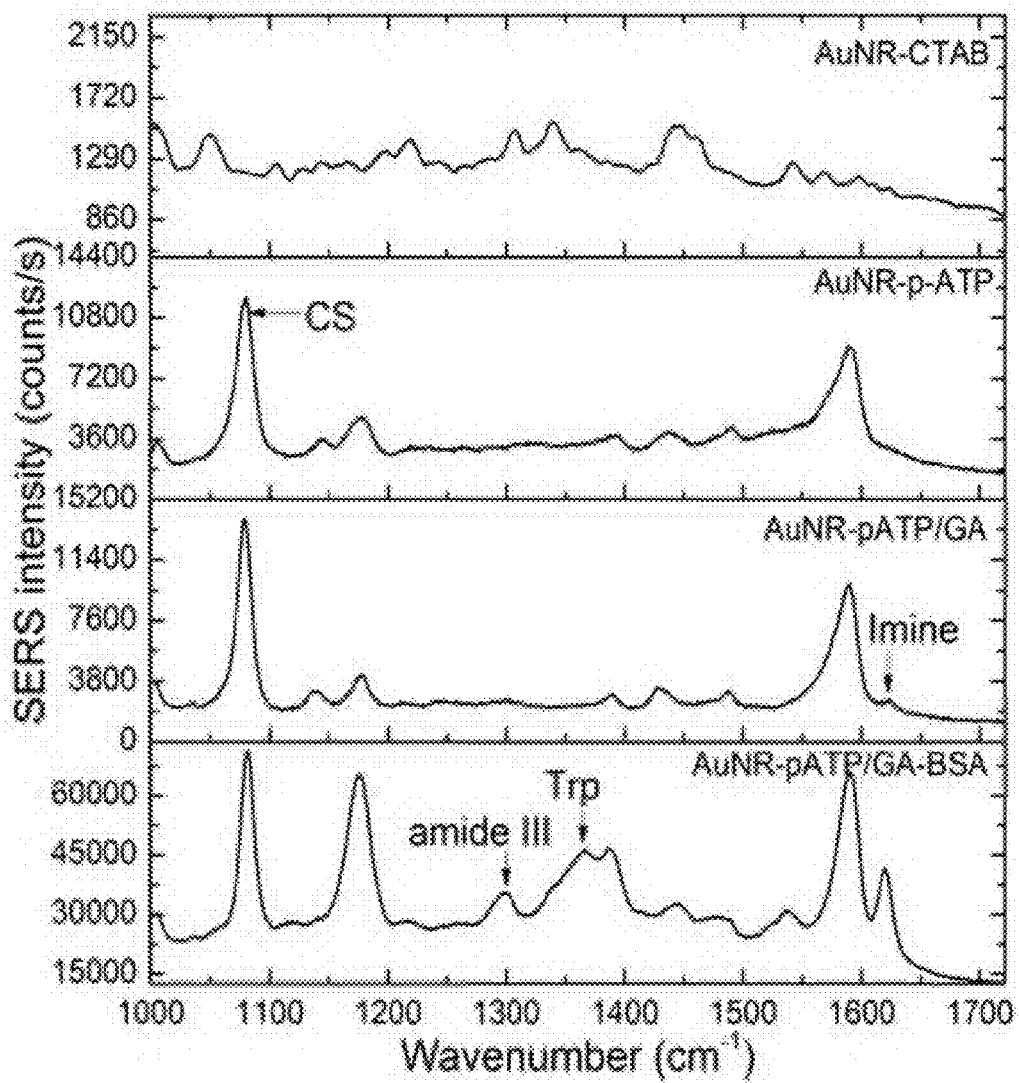
FIG. 9A is a graph summarizing the surface enhanced Raman scattering (SERS) spectra obtained from the AuNR at each step of the imprinting process.
Figure 9B:
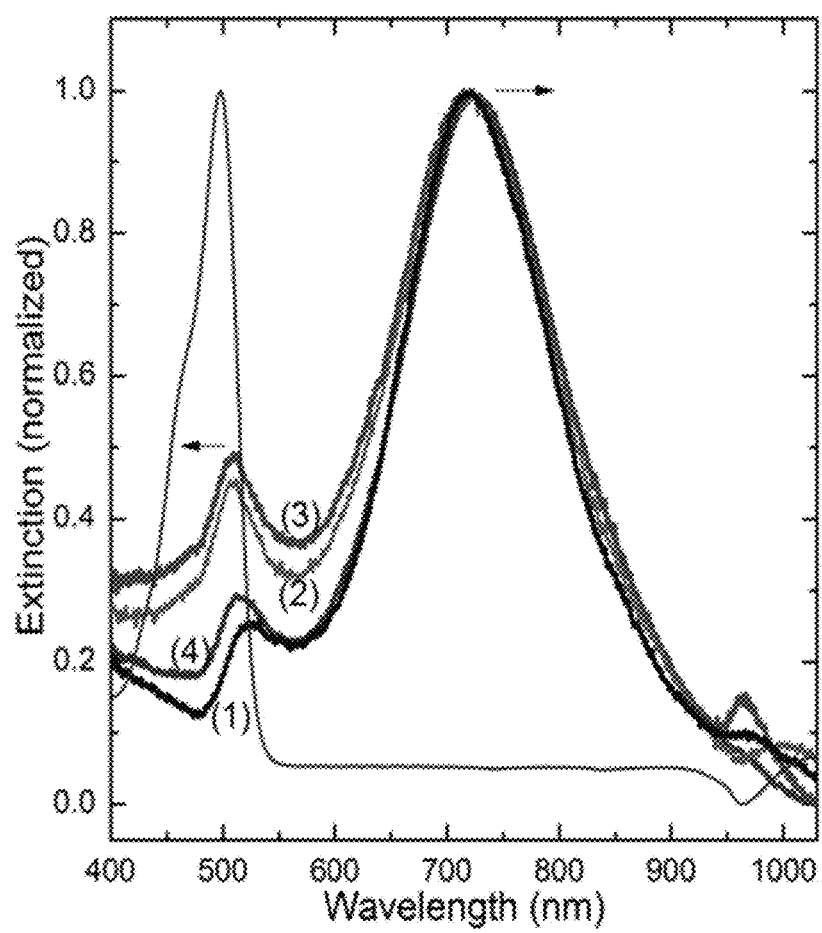
FIG. 9B is a graph summarizing the normalized extinction spectra of fluorescein-conjugated BSA (f-BSA) at 498 nm (purple) and AuNR before (1) and after immobilization of the template f-BSA (2), followed by a treatment with oxalic acid (3) or a mixture of oxalic acid and SDS (4) to release the template molecule.

FIG. 9 depicts the characterization of protein immobilization and release. FIG. 9A depicts the surface enhanced Raman scattering spectra obtained from the AuNR at each step of the imprinting process. FIG. 9B depicts the normalized extinction spectra of fluorescein-conjugated BSA (f-BSA) at 498 nm and AuNR before (line 1) and after immobilization of the template f-BSA (line 2), followed by a treatment with oxalic acid (line 3) or a mixture of oxalic acid and SDS (line 4) to release the template. The arrows indicate the shift in opposite direction of the longitudinal (720 nm) and transverse (523 nm) plasmon bands. The exposure of the AuNRs to BSA solution results in a red shift of the longitudinal band by 5 nm as expected, while the transverse band undergoes an apparent blue shift by 10 nm. The apparent blue-shift is due to the effect of fluorophore absorption band localized at slightly lower wavelength.

The confirmation of the protein template attachment was achieved using fluorescein-conjugated BSA (f-BSA). This experiment was designed to ascertain that the shift in the resonance wavelength observed in LSPR spectroscopy was due to the protein template molecules. Fluorescein is a synthetic fluorophore with an absorption maximum at 497 nm and emission maximum at 521 nm in aqueous solution. Localization of the fluorophore absorption peak next to the transverse plasmonic band (at about 525 nm) makes it useful to detect the immobilization of the fluorescein-conjugated BSA on the nanorod surface by monitoring the fluorophore-induced changes of the extinction band (FIG. 9B). The results were in agreement with the previous results and confirmed the effectiveness of the template immobilization procedure and its monitoring by LSPR. This experiment also revealed that the treatment with oxalic acid resulted in a release of 20%±4% of the template (f-BSA). When a mixture of oxalic acid and Sodium dodecyl sulfate (SDS) was used, the template release improved to 58±4%.

The synthesis, deposition and functionalization of AuNRs were monitored through their UV-visible extinction spectra collected using Shimadzu 1800 spectrophotometer. TEM images were obtained using a field emission transmission electron microscope (JEM-2100F, JEOL) operating at an accelerating voltage of 200 kV. AFM images were acquired using a Dimension 3000 AFM system (Bruker) in tapping mode using a silicon nitride cantilever. The change in shape and thickness of the modified nanorods during the imprinting process was monitored by imaging the same nanorods after each step of the process. This was made possible by performing successive scans starting with a large 50 µm×50 µm scan size and ending with a 200 nm×200 nm scan size.

To further investigate the imprinting process, the chemical composition at the surface of plasmonic transducers after each step was analyzed by SERS spectroscopy. The functionalization of the AuNRs by p-ATP/GA and protein templates resulted in the appearance of specific bands for each component as shown in FIG. 9A. The functionalization of the AuNRs by p-ATP/GA resulted in the appearance of a specific band at 1083 $cm^{-1}$ corresponding to C—S stretching vibration with a contribution from C—N stretching of the amine group. The interaction of GA with p-ATP on one side and GA with the protein amine groups on the other side was evidenced by the appearance of the imine band at 1620 $cm^{-1}$ after mixing GA with p-ATP and the significant increase in intensity of the same band after addition of the protein. The presence of the proteins was also confirmed by specific bands at 524 $cm^{-1}$ and 724 $cm^{-1}$ due to stretching of disulfide bridges (S—S) and C—S stretching of cysteine respectively. The bands at 833 cm$^{-1}$, 1298 cm$^{-1}$ and 1365 cm$^{-1}$ were assigned to tyrosine, alpha helix of amide III and tryptophan, respectively.

The chemical composition of the imprinted gold nanorods was analyzed by comparing their surface enhanced Raman spectra collected using a Renishaw inVia confocal Raman spectrometer mounted on a Leica microscope with 50× objective (NA=0.90) in the range of 100-3200 cm$^{-1}$. A diode laser of 785 nm wavelength (0.5 mW) was used for sample excitation.

Example 4: Electromagnetic Modelling and Plasmonic Hot-Spots

FIG. 10 depicts hot spot-localized imprinting of AuNRs. FIG. 10A is a representative TEM image of AuNR. FIG. 10B is a cross-sectional view of the electric field distribution around AuNR at the extinction maximum of the longitudinal band (724 nm in FIG. 2E). The image was obtained by finite-difference time-domain (FDTD) modeling. FIG. 10C is a schematic illustrating the preferential growth of the siloxane co-polymer at the nanorods ends where the capping ligand (CTAB) is sparse. FIGS. 10B and 10C show the spatial matching of the imprinted area with the localization of the plasmonic hot-spots. FIG. 10D is an AFM image (scan size 400 nm×400 nm) depicting the peanut-shaped MIP-AuNRs, corresponding to the scheme in FIG. 10C. The line in FIG. 10D indicates the localization the height profile represented in FIG. 10E. These results demonstrated that the MIP-AuNR thickness is 3-5 nm higher at the ends than in the center of the nanorods.

Figure 10A:
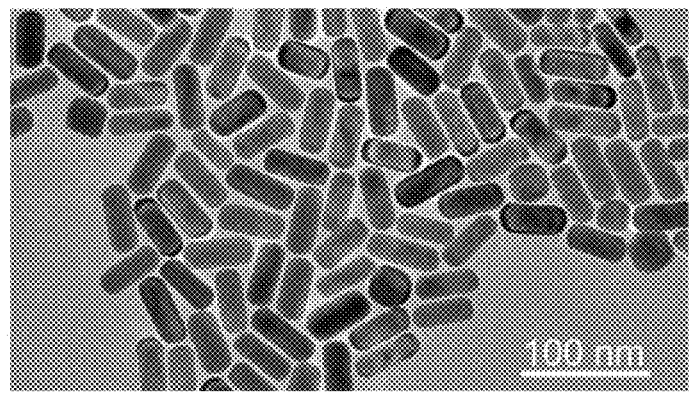
FIG. 10A is a TEM image of the gold nanorods.
Figure 10B:
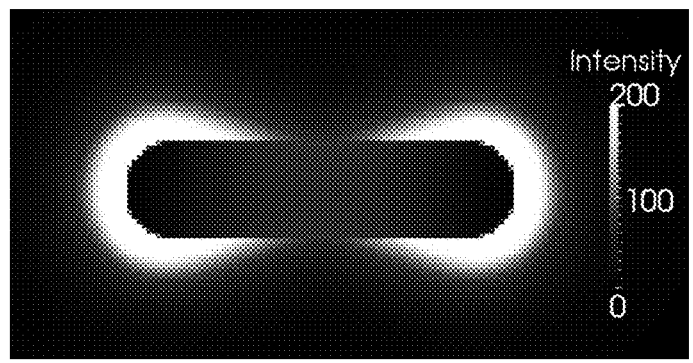
FIG. 10B is a cross-sectional view of the electric field distribution around a gold nanorod at the extinction maximum of the longitudinal band (724 nm).
Figure 10C:
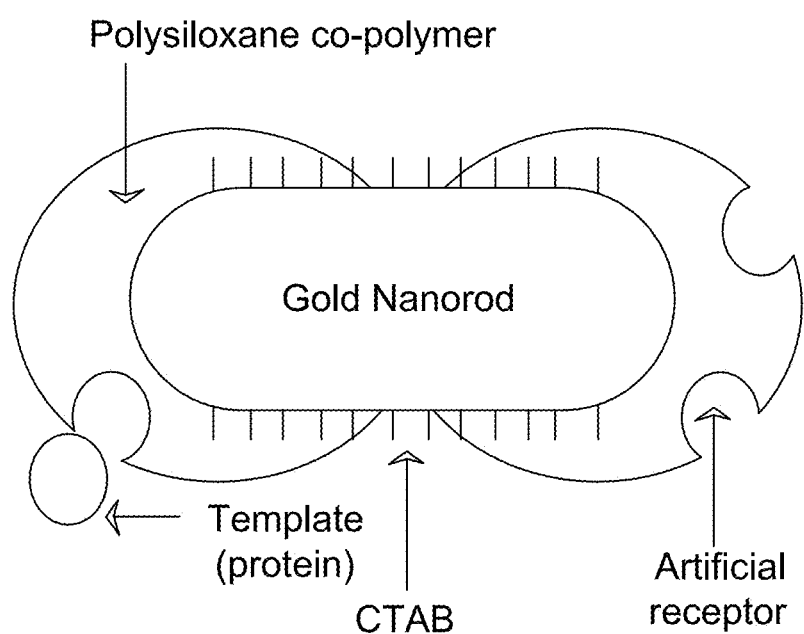
FIG. 10C is a schematic illustration showing the preferential growth of the siloxane co-polymer at the nanorods ends where the capping ligand (CTAB) is sparse.
Figure 10D:
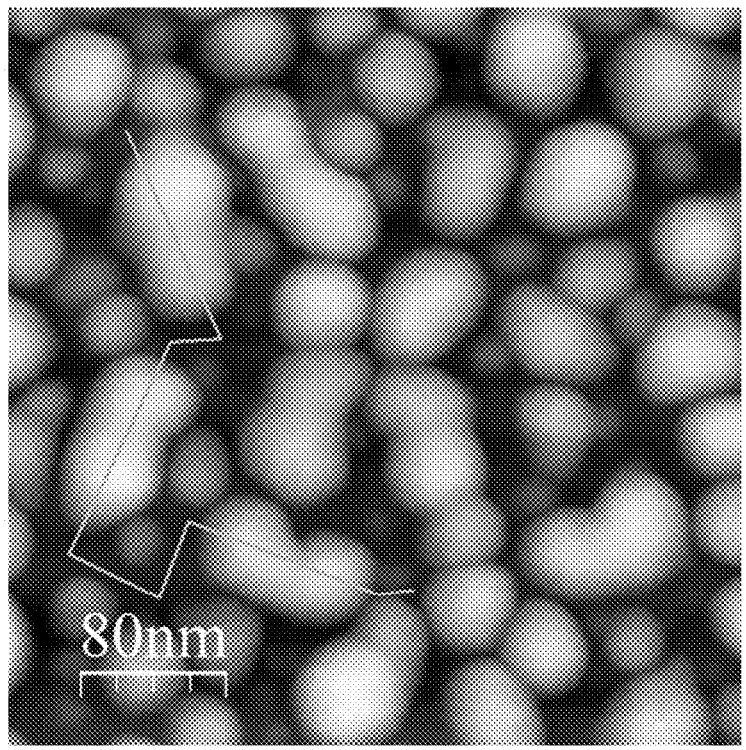
FIG. 10D is an AFM image (scan size 400 nm×400 nm) depicting the peanut-shaped molecularly imprinted gold nanorods.
Figure 10E:
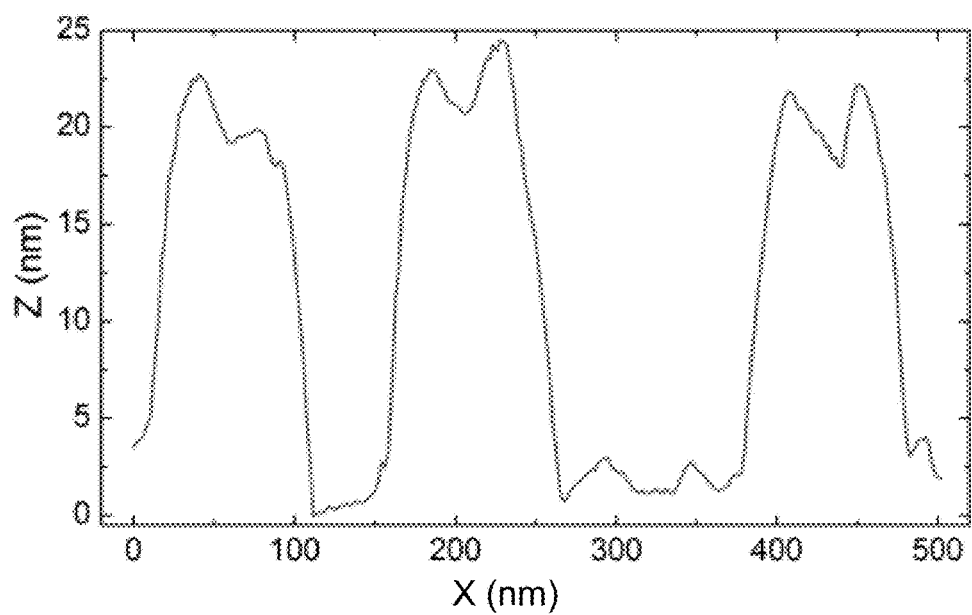
FIG. 10E is a graph of a height profile along the line superimposed on the AFM image of FIG. 10D.

A consideration in molecular imprinting of gold nanoparticles was the localization of the plasmonic hot-spots. The distribution and concentration of the electric field around AuNPs mostly depend on their shape. In the case of gold nanorods, the extinction spectrum exhibited a weak transverse (about 515 nm) and much stronger and more sensitive longitudinal (about 700 nm) plasmon resonances. The challenge was to favor the molecular imprinting at the nanorod ends at the plasmonic hot-spots (FIGS. 10A, B, and C). The peanut-shaped structures observed in the AFM image represented imprinted nanorods obtained by experimental conditions as discussed earlier (FIG. 10D). The unique shape was explained by the distribution of the capping ligand, i.e. CTAB molecules on the nanorod surface. Nanorod ends were much less covered with CTAB molecules as compared to the sides, which enabled their linear end-to-end assembly in some applications. The same property lead to a preferential adsorption of p-ATP/GA molecules at the nanorod ends and consequently to more available chemical anchors and faster growth of the siloxane polymer. The AFM profile showed that the siloxane polymer was about 3-5 nm thicker than that on the nanorods sides, which suggested that there was no significant film growth on the side-wall surface of the nanorods. As a result, the molecular imprinting of the template molecule was mainly localized at the plasmonic hot-spots, which provided a maximum sensitivity in LSPR-based detection.

The modeling of the electromagnetic field distribution around plasmonic nanorods was performed using three-dimensional finite-difference time-domain (FDTD) technique with commercially available software (EM Explorer). FDTD simulations exploit the time and position dependence of Maxwell's equations to model electromagnetic waves in rectangular 3D cells of finite volume called Yee cells. A single AuNR of 20 nm×80 nm size was modeled in a simulation domain of 300 nm×300 nm×200 nm. First, a wavelength scanning mode (300 nm-1100 nm) was performed to obtain the extinction profile of the nanorod using p-polarized incident plane wave for illumination. Perfectly matched layer (PML) absorbing boundary conditions were applied in all directions. Then, a higher resolution simulation (Yee cell size of 2 nm) was run at the extinction maximum wavelength (λ=724 nm) to obtain the electromagnetic field distribution. The complex refractive index of gold at this frequency was set to n=0.18+i 4.96.

Example 5: Template Rebinding and Reusability

Figure 11A:
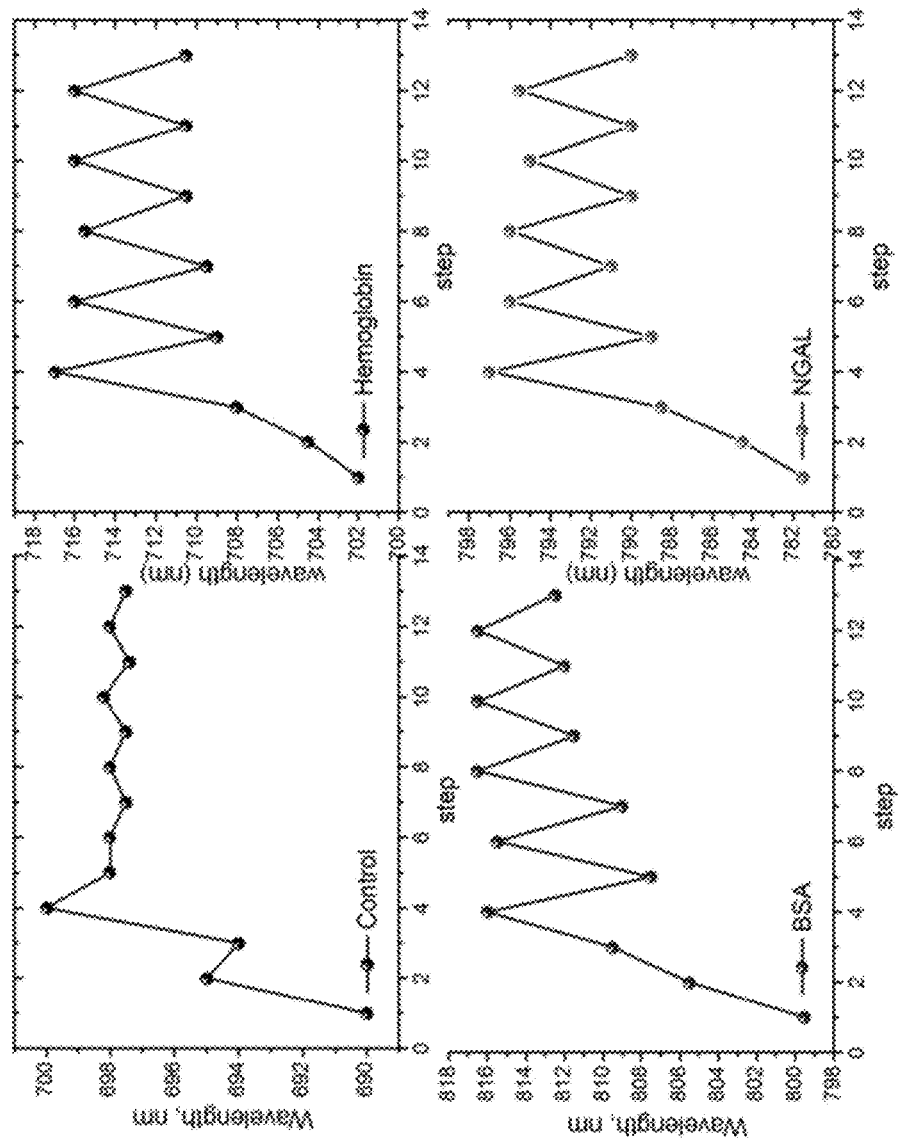
FIG. 11A is a graph summarizing the LSPR wavelength shifts of molecularly imprinted gold nanorods following successive steps of an imprinting methods in an aspect for three different target proteins.
Figure 11B:
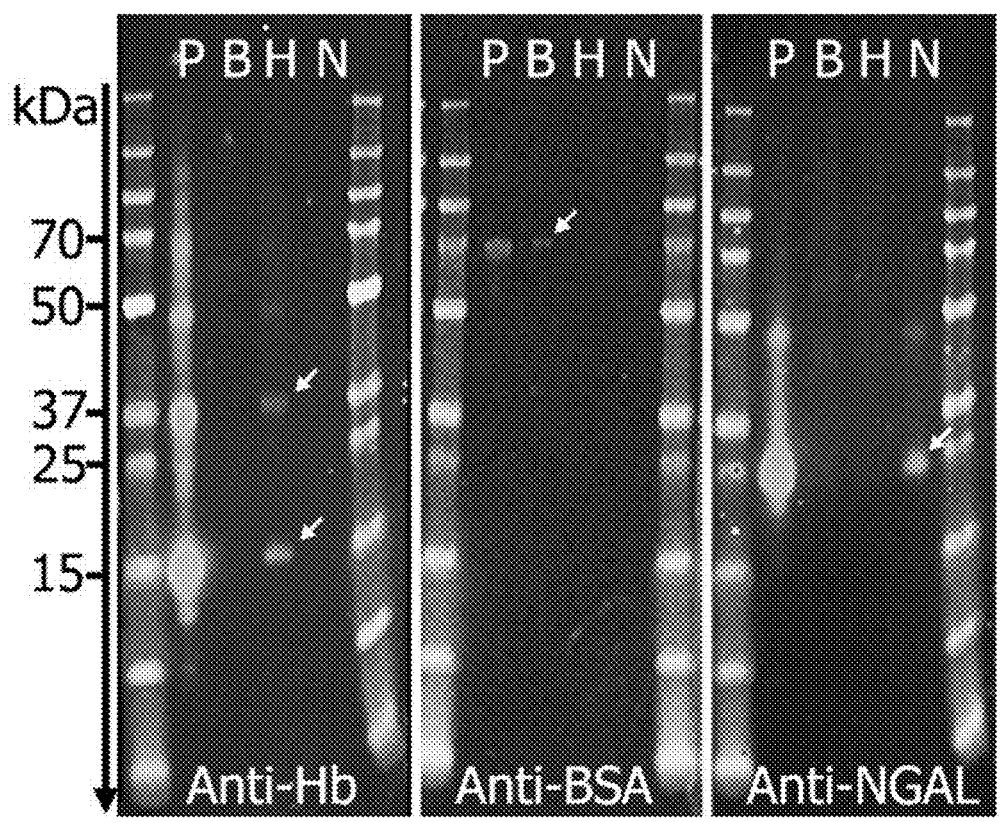
FIG. 11B are Western blotting images of the elute solutions obtained from the molecularly imprinted nanorod substrate prepared with 3 different protein templates: Bovine Hemoglobin (Hb), Bovine Serum Albumin (BSA) and recombinant human NGAL biomarkers. Each panel contains two molecular weight marker columns flanking 4 migration lanes: P is the protein mixture (containing Hb, BSA and NGAL) applied to all prepared molecularly imprinted gold nanorods. Lines B, H and N contain the elute solutions obtained from the MIP-AuNR substrates imprinted separately with BSA, Hb and NGAL respectively.

FIG. 11 shows the reproducibility and selectivity of the MIP-AuNR nanotransducers. FIG. 11A are graphs illustrating the shift of the LSPR wavelength following the different steps of the imprinting process. Each measurement point represents the shift obtained at the end of each step indicated with numbers. Steps 1 to 4 correspond to AuNR, AuNR-pATP/GA, AuNR-pATP/GA-protein and AuNR-pATP/GA-protein siloxane copolymer, respectively. At step 3, the control was exposed to PBS buffer solution without proteins. Steps 5 to 13 correspond to 4 cycles of protein capture and release, resulting in a red-shift or blue-shift, respectively. The same procedure is applied to hemoglobin, BSA and NGAL biomarker. The control was not treated with proteins. FIG. 11B depicts Western blotting of the elute solutions obtained from molecularly imprinted nanorod substrate prepared with 3 different protein templates: Bovine Hemoglobin (Hb), Bovine Serum Albumin (BSA) and recombinant human NGAL biomarkers. Each panel contains two molecular weight marker columns flanking 4 migration lanes: P is the protein mixture (containing Hb, BSA and NGAL) applied to all prepared MIP-AuNR substrates. Lines B, H and N contain the elute solutions obtained from the MIP-AuNR substrates imprinted separately with BSA, Hb and NGAL respectively. The treatment with the antibody Anti-Hb, revealed 2 clearly identified bands in the H lane indicating the presence of denatured Hb with a single sub-unit (~17 kDa) or two sub-units (~37 kDa). A weak band at ~50 kDa indicated the presence of a 3 sub-units Hb. The second panel treated with anti-BSA revealed a weak band at ~70 kDa demonstrating the presence of BSA. The anti-NGAL treatment of the last paned showed a clear band at ~25 kDa, corresponding to the molecular weight of NGAL. A weak band was also observed at ~45 kDa indicating the presence of NGAL concatemers due to a small amount of recombinant NGAL resulting from plasmid concatemerization.

To demonstrate the template molecule rebinding, reproducibility and reusability of the imprinted plasmonic nanotransducers, three different nanorod-coated glass substrates were imprinted with BSA, hemoglobin or NGAL proteins. A fourth sample that underwent the same imprinting procedure but without using protein template molecules was used as a control. As shown by the extinction spectra in FIG. 11A, the accumulated shift due to the imprinting process was about 16 nm. This was observed for all the samples except the control that showed a shift of about 10 nm. This was expected as no protein template molecule was used in this sample. Instead of a red-shift, a blue-shift was observed for the control sample at step 2 (FIG. 11A), which was likely due to a loss of weakly adsorbed material (CTAB, GA) after 2 h of incubation in PBS buffer. Likewise, the first release of the template in the different samples suggested that the protein template removal was accompanied by the loss of weakly polymerized siloxane, leading to a blue-shift of about 8 nm rather than the expected shift of about 5 nm for protein removal. Cycles of protein capture and release showed a better stability of the imprinted AuNR surface and demonstrated excellent reproducibility for all proteins used. The shifts induced by the capture/release cycles were around 5 nm for the molecularly imprinted supports, while they were 10 times smaller for the control, demonstrating a very good efficiency of the artificial antibodies. The small shifts observed for the control were mostly caused by non-specific adsorption of the protein. The same results were obtained with two other proteins, i.e., immunoglobulin G (IgG) and allophycocyanin.

Example 6: Competitive and Cross-Binding Experiments

The competitive binding experiment was performed by immersing each of the three imprinted sensors (MIP-NGAL, MIP-BSA and MIP-Hb) in a mixture of proteins containing 0.5 mg/mL BSA, 0.5 mg/mL Hb and 0.5 mg/mL NGAL and incubated for 30 min at room temperature. The sensors were then washed with PBS buffer in three different baths for 5 min each and under gentle shaking. After thorough rinsing, the proteins were released and the elute solutions were separately analyzed by Western blotting (FIG. 11B). Each sensor substrate was separately exposed to a mixture of SDS (2%) and oxalic acid (2 mM) for 30 min under gentle shaking, and the eluate was analyzed by Western-blotting. The cross-binding experiment was performed by successively exposing each imprinted sensor in 0.5 mg/mL NGAL, BSA and Hb for 30 min each. After each treatment, the shift in the maximum resonance wavelength was monitored using a UV-visible spectrometer (FIG. 12).

Figure 12:
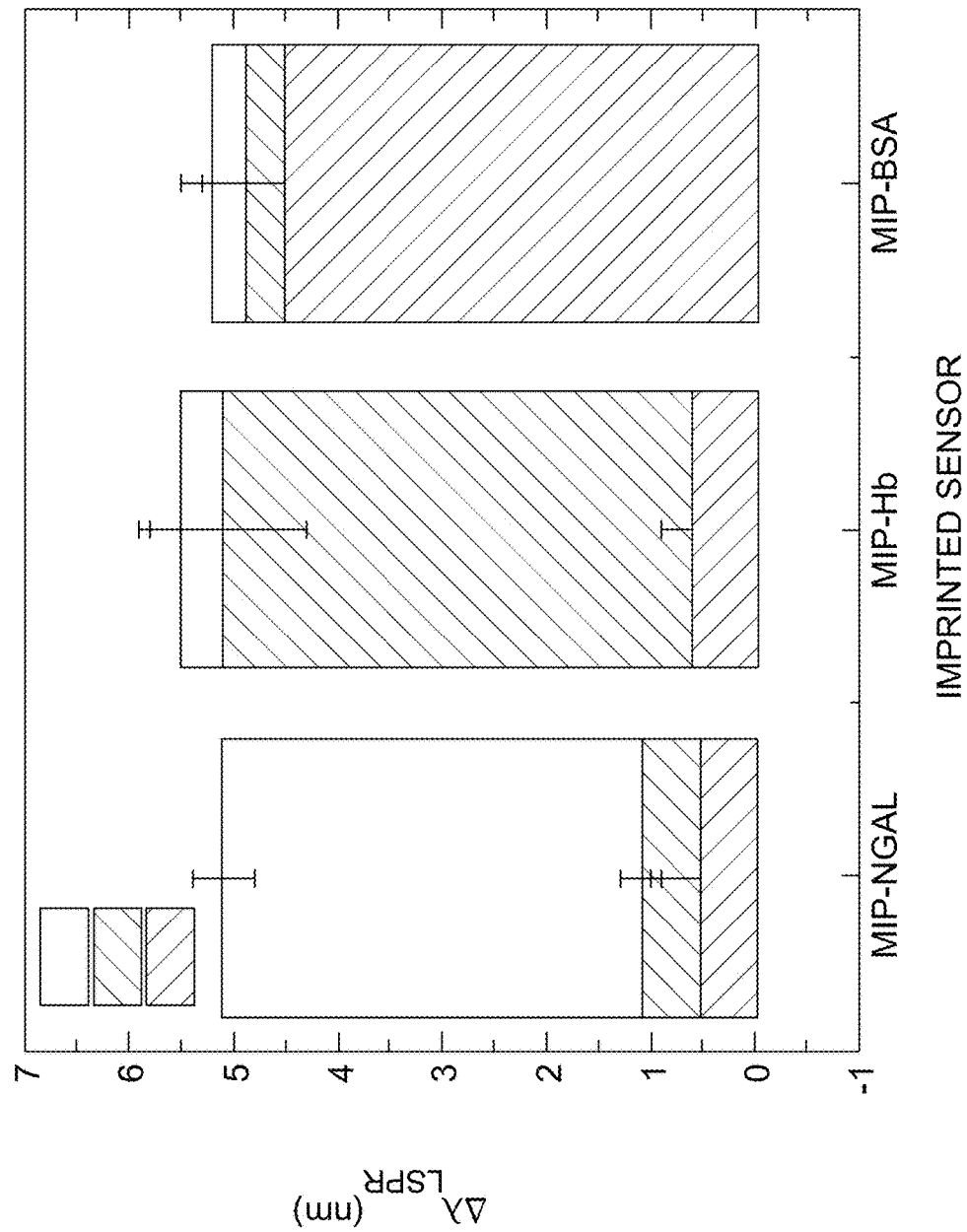
FIG. 12 is a bar graph summarizing the cross-binding characteristics of gold nanorods molecularly imprinted using three different protein templates.

FIG. 12 shows a cross-binding experiment for the evaluation of non-specific adsorption. The sensors imprinted with three different proteins (MIPNGAL, MIP-Hb and MIP-BSA) were separately and successively exposed to NGAL, Hb and BSA proteins and the induced LSPR wavelength shift was monitored. Despite exposing the MIP-AuNR substrates to a mixture of three different proteins, only one protein was recognized in each panel, which corresponded to the template used for imprinting. This agreed with the LSPR measurements performed with the imprinted sensors on different protein mixtures. The LSPR shift of the extinction spectra also accompanied an increase in the full width at half maximum (FWHM). Both Western blotting and LSPR results demonstrated the high specificity and selectivity of the imprinted plasmonic nanotransducers. The cross-binding experiment also assessed the contribution of non-specific protein adsorption by separately and successively exposing the three imprinted plasmonic nanotransducers to each protein (FIG. 12). The results showed that non-specific binding induced a shift of less than 1 nm in all cases, which indicated a relatively low level of adsorption.

Western blotting was performed on the samples. Samples of the initial applied mixture of the 3 proteins and each specific eluate (30 μL) were mixed with 10 μL of 4×SDS sample buffer (LI-COR Biosciences, Lincoln, Nebr.) containing mercaptoethanol and heated at 90° C. for 10 min. The sample representing the applied protein mixture was further diluted 10-fold with 1×SDS sample buffer. Five μL of each sample was applied to a 17-well 4-12% acrylamide BIS-TRIS gel (Invitrogen) and electrophoresed for 32 min at 200V, and the proteins transferred to nitrocellulose using an i-BLOT (Invitrogen Life Technologies, Grand Island, N.Y.). The membrane was blocked in LI-COR blocking buffer, cut into segments, and incubated with antibodies specific to mouse albumin (abcam, Cambridge, Mass.) rabbit anti-mouse antibody that detects human serum albumin and that of other species with less affinity $^{1}/_{10,000}$, human hemoglobin (R&D Systems, Minneapolis, Minn.) goat antibody 0.2 μg/ml, or human NGAL (R&D Systems, Minneapolis, Minn.) goat antibody 0.2 μg/ml; each diluted in LI-COR blocking buffer containing 0.1% Tween-20 (Sigma Chemical Company, St. Louis, Mo.) overnight. Membranes were washed 3 times in phosphate buffered saline (PBS) containing 0.1% Tween-20 and each membrane was incubated with donkey anti-rabbit IgG IRDye 680 or donkey anti-goat IgG IRDye 800 (LI-COR Biosciences, Lincoln, Nebr.) as appropriate for 1 h. The membranes were washed 3 times as above, one time with PBS, and visualized using an Odyssey Infrared Imager (LI-COR Biosciences, Lincoln, Nebr.).

Example 7: Application of AuNR Nanotransducer

Figure 13:
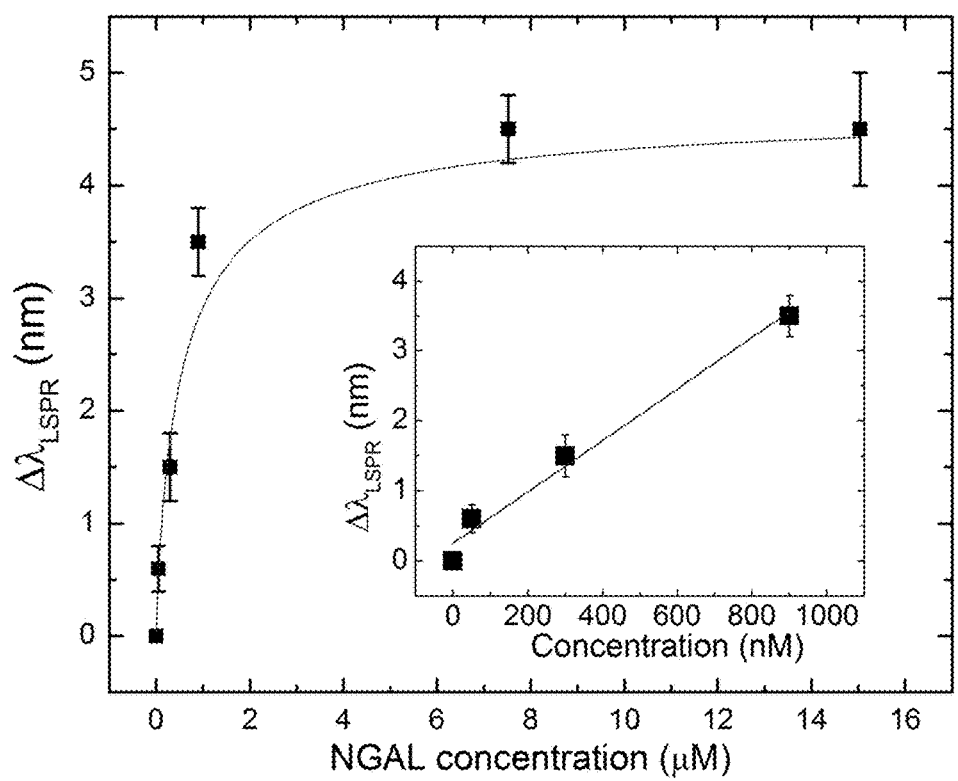
FIG. 13 is a graph summarizing the LSPR wavelength shift as a function of NGAL concentration.

To complete the analytical investigation of the molecularly imprinted nanorods, different concentrations of NGAL were used to evaluate the detection sensitivity. FIG. 13 shows the sensitivity of the MIP-AuNR nanosensor expressed by the shift in the LSPR wavelength in nm as a function of NGAL concentration in μM. The data were fitted with an exponential decay function. The linear fit (in the inset) could be applied for protein concentrations lower than 1 μM, providing a sensitivity of 0.6 nm/μM (R2=0.98). FIG. 13 shows that a plateau was reached at concentrations higher than 16 NM (400 μg/mL). However, a linear relationship could be applied to concentrations lower than 1 μM. This dynamic range provided a LSPR sensitivity of 0.25 nm/nM and a detection limit of 13 nM or 0.32 μg/mL of NGAL (the wavelength precision of the optical detection system was ±0.1 nm). This performance surpassed that provided by the molecular imprinting using other traditional techniques such as quartz crystal microbalance and liquid chromatography, and was suitable for the detection of many proteins at clinical concentrations including NGAL biomarkers after kidney injury.

Figure 14:
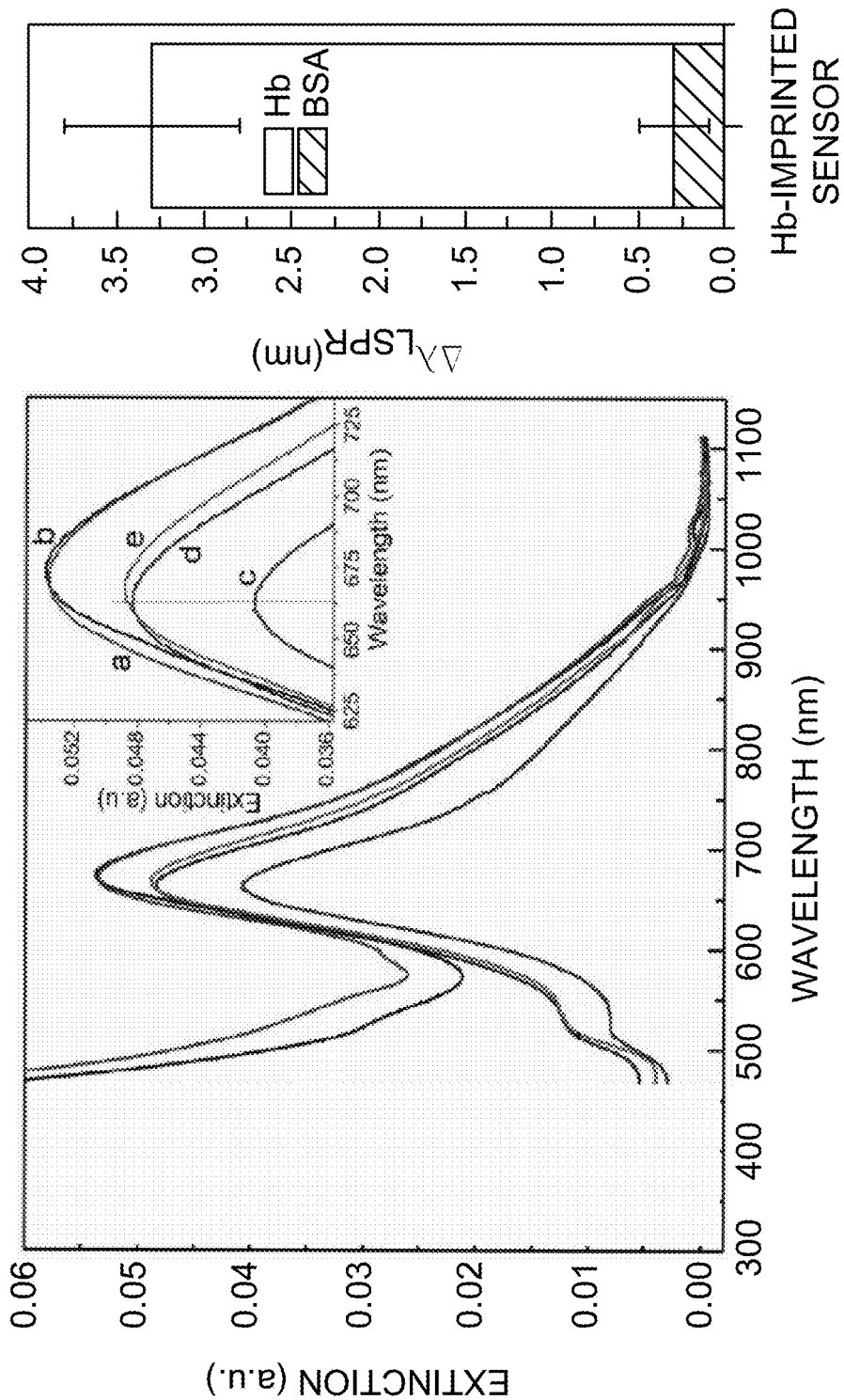
FIG. 14 is an graph summarizing the extinction spectra of the sensor substrate during incubation in urine sample before (A) and immediately after (B) addition of 30 μg/mL hemoglobin, as well as after incubation in normal urine (C) or after incubation in a urine sample containing BSA (D), or after incubation in a urine sample containing hemoglobin (E). The diagram on the right depicts the shift in the maximum wavelength of the Hb-imprinted nanorods after exposure to urine containing either Hemoglobin or BSA.

FIG. 14 shows the application of AuNR-imprinted sensors for the detection of hemoglobin in a real urine sample. FIG. 14A is an image of the sensor substrate during incubation in urine sample. Lines (a) and (b) represent respectively the extinction spectra of the sensor immersed in cuvette (A) before and immediately after addition of 30 μg/mL hemoglobin. After incubation in urine sample without or with the presence of target proteins, the sensor is washed and immersed in water (cuvette B) for LSPR analysis. The graphs (Lines c-e) represent respectively the extinction spectra of the sensor substrate after incubation in normal urine (Line c) or after incubation in urine sample containing either BSA (Line d) or hemoglobin (Line e). The diagram on the right depicts the shift in the maximum wavelength of the Hb-imprinted nanorods after exposure to urine containing either Hemoglobin or BSA.

To further demonstrate the implementation of the imprinted AuNR sensors in real-world and complex samples, hemoglobin detection was performed in a normal urine sample (FIG. 14). Hemoglobinurea is a pathological condition exhibited by the presence of hemoglobin in urine, which can lead to acute tubular necrosis. An Hb-imprinted sensor was first immersed in a urine solution to study the effect of this complex sample containing a variety of organic and inorganic components on the extinction spectrum. As shown in FIG. 14, the longitudinal peak at λ≈662 nm used for sensing remains intact, while the transverse peak was overlapped by the huge absorbance of urine at λ<500 nm. This absorbance was caused by urine pigments including urobilin which was the final product of heme breakdown. To decrease the effect of this absorbance/fluorescence on the plasmon resonance peaks, the urine sample was diluted 5 times before use. The AuNR sensor was then incubated in a urine sample containing 30 μg/mL of either hemoglobin or BSA. After washing with distilled water, the extinction spectra of the sensors were obtained in water. The results showed a significant LSPR shift for hemoglobin ($\Delta\lambda=3.5$ nm±0.5 nm), while the change caused by BSA remained insignificant ($\Delta\lambda<0.5$ nm). This demonstrated the successful specific capture of hemoglobin by the imprinted nanorods the feasibility of antibody-free plasmonic biosensing for real-world applications.

Example 8: Synthesis of Silver Nanocubes and Gold Nanocages (AuNCs)

This example illustrates the methods used for the synthesis of AuNCs and AgNCs.

Ethylene glycol (Lot. no K26B01) and sodium sulfide ($Na_2S$) were purchased from J. T. Baker. Cetyltrimethylammonium bromide (CTAB), ascorbic acid, sodium borohydride, poly(styrene sulfonate) (PSS) (MW=70,000 g/mol), and poly(allyl amine hydrochloride) (PAH) (MW=56,000 g/mol), sodium borohydride ($NaBH_4$), Silver nitrate (purity higher than 99%), 4-aminothiophenol (pATP), glutaraldehyde (GA), poly(vinyl pyrrolidone) (PVP, MW-29,000), chloroauric acid ($HAuC_{14}$), myoglobin from human heart (MW=17.7 kDa), hemopexin from human plasma (MW=57 kDa), α1-antitrypsin from human plasma (MW=52 kDa), α1-acid glycoprotein from human plasma (MW=40.8 kDa), albumin from human serum (MW=66.5 kDa), and hemoglobins human (MW=64.5 kDa) were obtained from Sigma-Aldrich. Sucrose was purchased from G-Biosciences Inc. Poly(2-vinyl pyridine) (MW=200,000 g/mol) was obtained from Scientific Polymer Products Inc. Artificial urine was purchased from Cerilliant Corp. Recombinant human fatty acid-binding protein 1 (FABP1) (MW=14.2 kDa), and recombinant human fatty acid binding protein-3 (FABP3) (MW=14.8 kDa) were obtained from RayBiotech, Inc. Recombinant neutrophil gelatinase associated lipocalin was obtained from SunnyLab (Kent, United Kingdom). All the chemicals were used as received with no further purification.

Transmission electron microscopy (TEM) micrographs were recorded on a JEM-2100F (JEOL) field emission instrument. Samples were prepared by drying a drop of the solution on a carbon-coated grid, which had been previously made hydrophilic by glow discharge. Scanning electron microscope (SEM) images were obtained using a FEI Nova 2300 Field Emission SEM at an accelerating voltage of 10 kV. Shimadzu UV-1800 spectrophotometer was employed for collecting UV-vis extinction spectra from solution and substrates.

Prior to synthesis, all the glassware was cleaned using aqua regia (3:1 volume ratio of 37% hydrochloric acid and concentrated nitric acid). Silver nanocubes were synthesized using a sulfide-mediated method developed previously. Briefly, 90 μL of $Na_2S$ solution (3 mM) in ethylene glycol was added to 6 ml of preheated ethylene glycol at 160° C. in a disposable glass vial. After 8 min, 1.5 ml of PVP (0.02 g/ml) in ethylene glycol was added to the above mixture, immediately followed by the addition of 0.5 ml of $AgNO_3$ (0.048 g/ml) in ethylene glycol. The reaction was complete in 10 min with a dark ruddy-red meniscus in reaction solution. The product was washed with acetone and water by centrifugation. 10 ml of aqueous PVP solution (9 mM) was add to 1 ml of the above mentioned silver nanocubes solution. After bringing the suspension to a mild boil for approximately 10 min, 1 mM $HAuC_{14}$ was injected at a rate of 0.5 ml/min under vigorous stirring until dark blue color appeared. The AuNC product was centrifuged once and redispersed in nanopure water before using (18.2 MΩ-cm).

Example 9: Synthesis of Gold Nanorods

This example illustrates the methods used for the synthesis of AuNRs.

Gold nanorods were synthesized using a seed-mediated approach. Seed solution was prepared by adding 0.6 mL of an ice-cold solution of 10 mM sodium borohydride into 10 mL of vigorously stirred 0.1M CTAB and $2.5\times10^{-4}$M $HAuC_{14}$ aqueous solution at room temperature. The color of the seed solution changed from yellow to brown. Growth solution was prepared by mixing 95 mL of 0.1M CTAB, 1.0 mL of 10 mM silver nitrate, 5 mL of 10 mM $HAuC_{14}$, and 0.55 mL of 0.1M ascorbic acid in the same order. The solution was homogenized by gentle stirring. To the resulting colorless solution, 0.12 mL of freshly prepared seed solution was added and set aside in dark for 14 h. Prior to use, the AuNRs solution was centrifuged at 13,000 rpm for 10 min to remove excess CTAB and redispersed in nanopure water.

Example 10: Need for Plasmonic Nanotransducers with High Refractive Index Sensitivity This example demonstrates the need for artificial antibodies in addition to a higher refractive index sensitivity and optimal decay length. Gold nanorods (AuNRs) were synthesized using the method described in Example 2.

Gold nanorods, with built-in artificial antibodies by molecular imprinting (see Example 7), were used to detect a kidney injury biomarker (neutrophil gelatinase-associated lipocalin, NGAL). The AuNRs were able to detect NGAL down to a concentration of 320 ng/ml. However, the limit of detection achieved with AuNRs was higher than the physiologically relevant concentration of NGAL in urine (50-300 ng/ml). These considerations suggested the need for plasmonic nanotransducers with higher refractive index sensitivity and optimal electromagnetic decay length.

Example 11: Comparison of Plasmonic Nanotransducers Using Gold Nanocages

In this Example, the bulk and distance-dependent refractive index sensitivity of AuNRs and AuNCs were determined and compared. The former nanostructures have been studied and employed as plasmonic nanotransducers due to the facile and large tunability of the LSPR wavelength and their higher refractive index sensitivity (about 200 nm/RIU) compared to gold nanospheres (40-60 nm/RIU).

AuNCs were obtained by galvanic replacement of Ag nanocubes with gold using $HAuC_{14}$, as described in Example 1. Ag nanocubes were synthesized according to a sulfide-mediated polyol synthesis method. The synthesis reaction was quenched once the dipolar LSPR wavelength of the silver nanocubes reached about 430 nm, which yielded nanocubes with an edge length of about 50 nm.

Figure 1C:
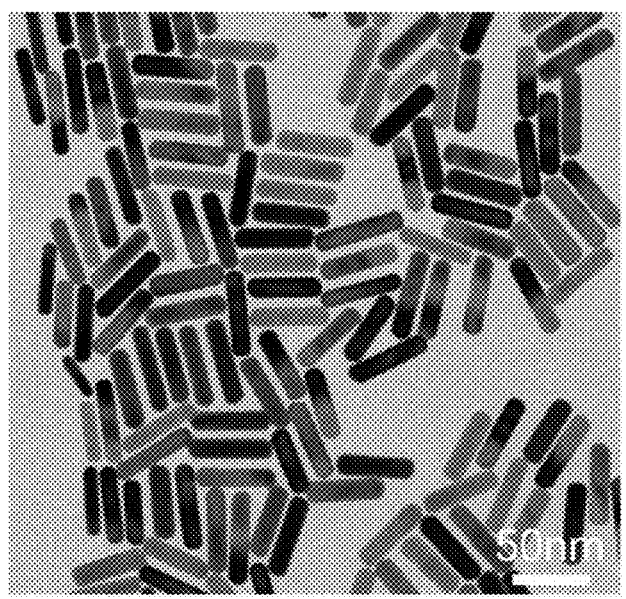
FIG. 1C is a TEM image of gold nanorods.
Figure 1B:
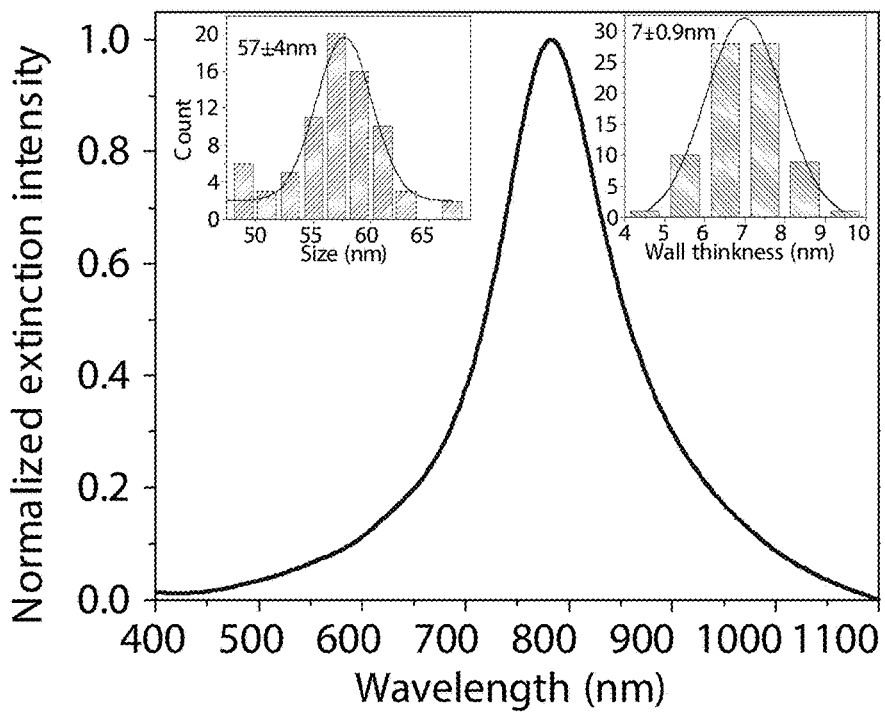
FIG. 1B is a Vis-NIR extinction spectrum and size distribution for the gold nanocages shown in FIG. 1A.
Figure 1D:
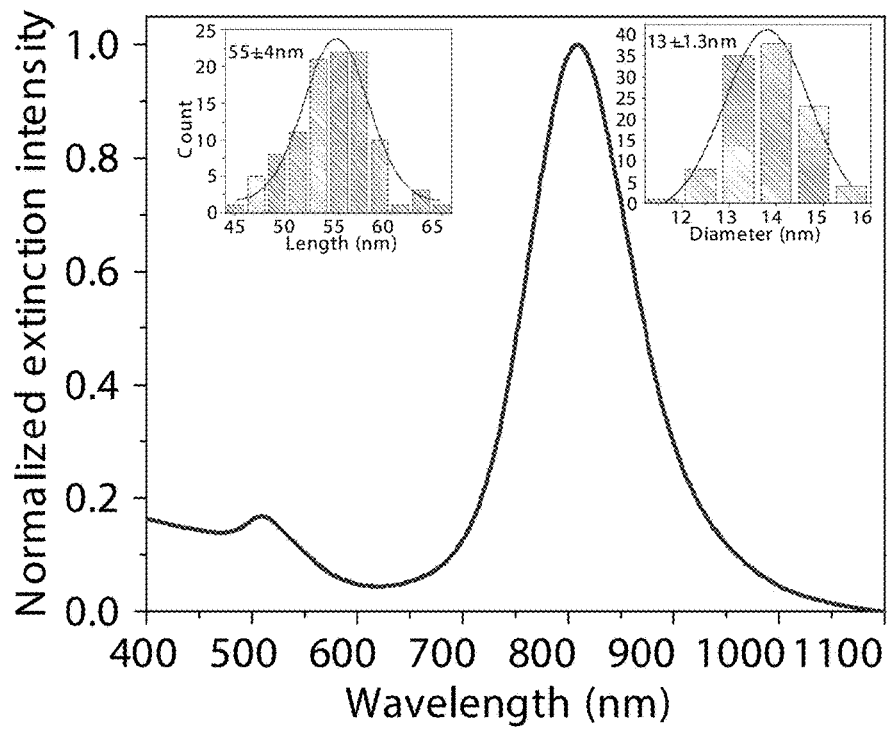
FIG. 1D is a Vis-NIR extinction spectrum and size distribution for the gold nanorods shown in FIG. 1C.

FIG. 1A is a TEM image of Au nanocages (inset is a high magnification image revealing the pores on the surface of walls. Scale bar: 20 nm). FIG. 1B is a vis-NIR extinction spectrum of the aqueous suspensions of Au nanocages. FIG. 1C is a TEM image of Au nanorods. FIG. 1D is a vis-NIR extinction spectrum of the aqueous suspensions of Au nanorods (inset shows the histogram of the size distribution as measured from TEM images). The AuNCs, which exhibited a LSPR wavelength of 783 nm, had an outer edge length of 57±4 nm and a wall thickness of 7±0.9 nm. The TEM image of the AuNCs revealed the hollow nanostructures with porous sidewalls having an average pore size of about 4 nm. AuNRs, synthesized using a seed-mediated approach, were positively charged with a length of 55±4 nm and a diameter of 13±1.3 nm. The extinction spectrum of AuNRs solution showed the characteristic transverse and longitudinal surface plasmon resonances of AuNRs associated with the oscillation of conduction electrons in transverse and longitudinal directions of the nanorods. The refractive index sensitivity of a wide variety of plasmonic nanostructures scaled roughly linearly with LSPR wavelength. To ensure a fair comparison of refractive index sensitivities between AuNRs and AuNCs, the aspect ratio of AuNRs was chosen so that the longitudinal plasmon resonance wavelength of AuNRs in solution (810 nm) was close to the plasmon band of AuNCs in solution (783 nm).

Example 12: Adsorption of AuNCs on Glass Surface

This Example demonstrated the adsorption (immobilization) of AuNCs onto a glass surface.

To adsorb gold nanocages onto glass substrates, the glass substrates were coated with poly(2-vinyl pyridine) (P2VP) by exposing the piranha cleaned substrates to 1% (w/v) P2VP solution in ethanol. The pyridyl groups of P2VP have a high affinity for gold, resulting in strong adsorption of AuNCs to P2VP film. After rinsing the substrate with ethanol and drying with a stream of nitrogen, it was exposed to a AuNCs solution overnight to adsorb the gold nanocages to the substrate. The substrate was then rinsed with water to remove the loosely bound nanocages, leaving a highly dense layer of nanocages on the surface.

Figure 2A:
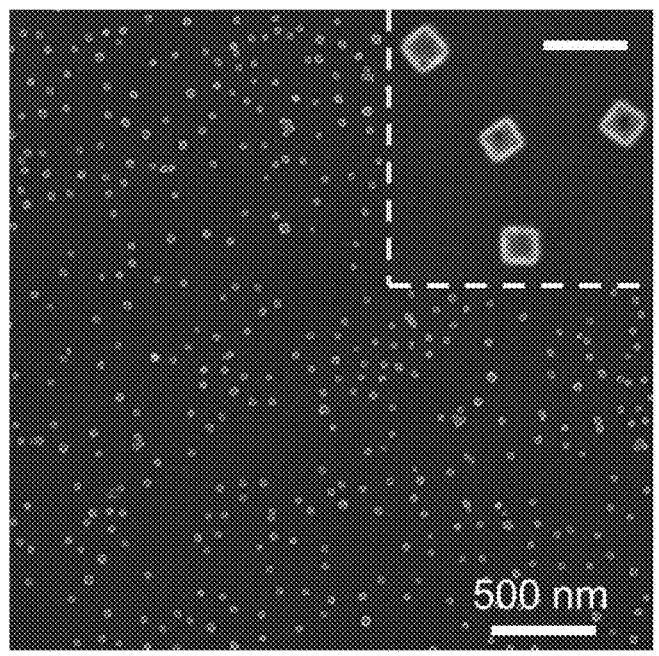
FIG. 2A is a scanning electron micrograph (SEM) image of Au nanocages adsorbed on a glass substrate.
Figure 2B:
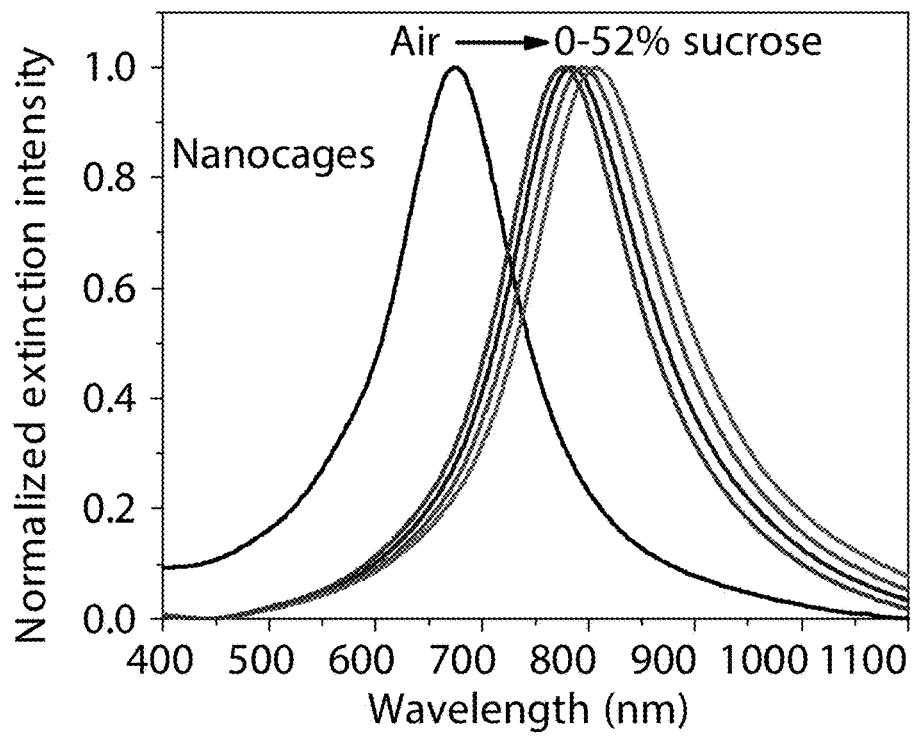
FIG. 2B is the Vis-NIR extinction spectra of the Au nanocages shown in FIG. 2A in air and different concentrations of sucrose aqueous solution.
Figure 2C:
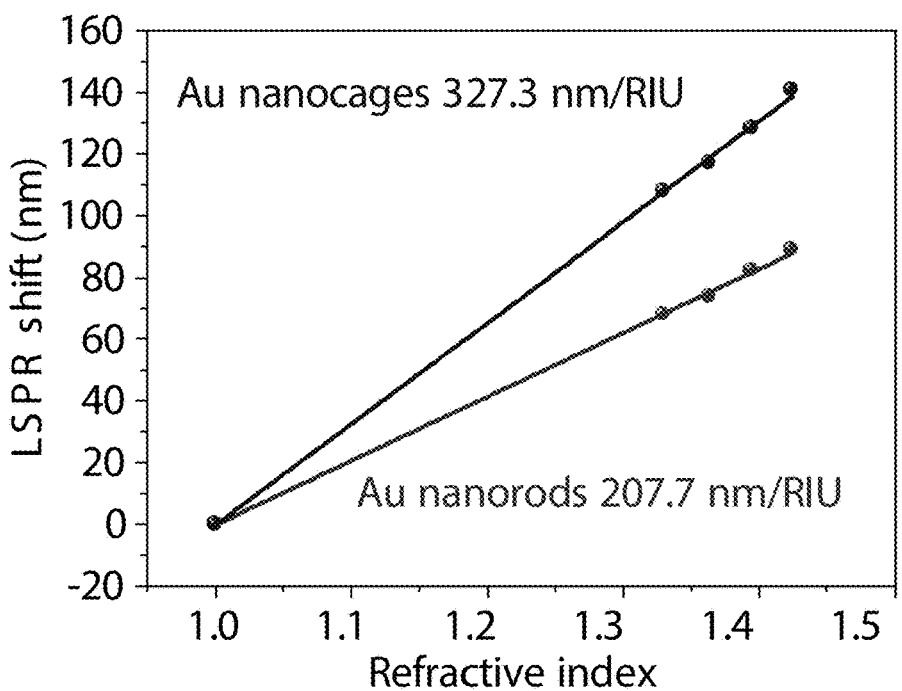
FIG. 2C is a comparison of the bulk dependent refractive index sensitivity of Au nanocages and nanorods.
Figure 2D:
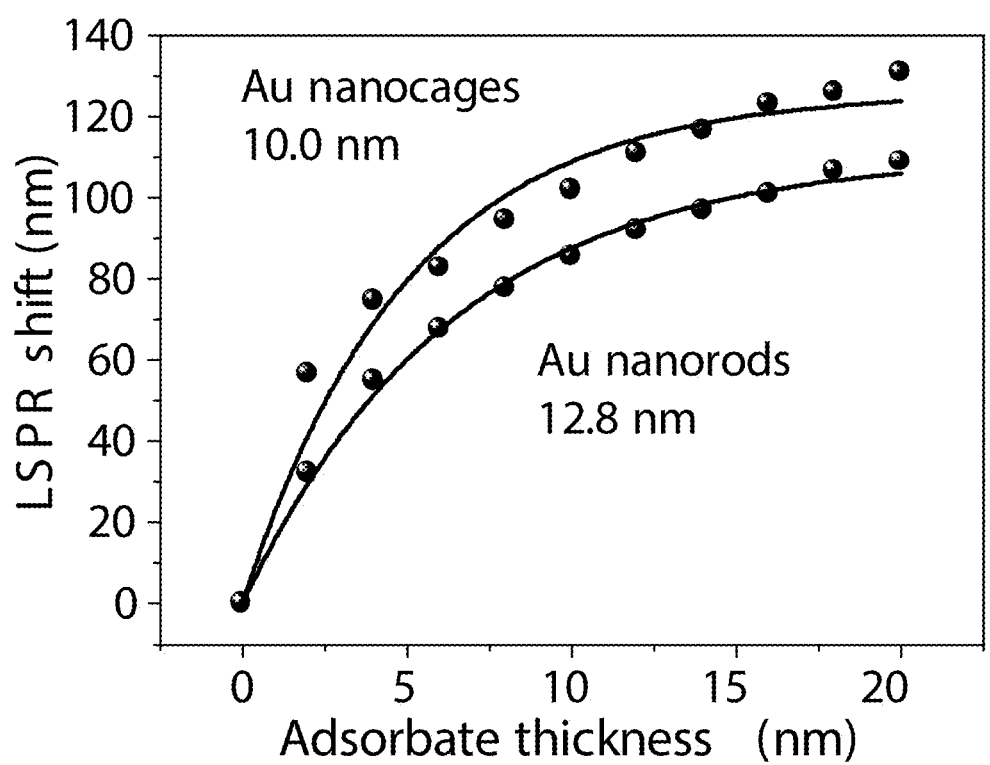
FIG. 2D is a comparison of the distance-dependent refractive index sensitivity of Au nanocages and nanorods.

FIG. 2A is an SEM image of Au nanocages adsorbed on a glass substrate. The SEM images revealed the uniform distribution of AuNCs with no signs of aggregation or patchiness. The same procedure described above was employed to adsorb AuNR on glass substrates. To probe the bulk refractive index sensitivity of AuNCs and AuNRs, extinction spectra were collected by changing the refractive index of surrounding medium. FIG. 2B is the Vis-NIR extinction spectra of Au nanocages in air and different concentrations of sucrose aqueous solution. The spectra revealed a progressive red-shift in LSPR wavelength with increase in the refractive index of surrounding medium (from air to different concentration of sucrose solutions). FIGS. 2C and 2D illustrate the comparison of bulk and distance dependent refractive index sensitivity of Au nanocages and nanorods.

The extinction band of AuNCs and AuNRs deposited on glass surface exhibited a small shoulder at higher wavelength due to the plasmon coupling between the nanostructures. The extinction spectrum was deconvoluted by fitting the band with two Gaussian peaks, from which the LSPR wavelength was obtained. The peak corresponding to the dipolar resonance of individual AuNCs was employed to probe the refractive index sensitivity. The refractive index sensitivity of AuNCs was found to be 327.3 nm/RIU, which was about 58% higher than that of the longitudinal plasmon band of AuNRs (about 207 nm/RIU), as seen in FIG. 2C. High refractive index sensitivity (RIS) was also reported for Au nanostars (703 nm/RIU for plasmon wavelength 1141 nm) and nanobipyramids (392 nm/RIU for LSPR wavelength 886 nm). The polydispersity in the shape of these nanostructures resulted in broad LSPR bands, which severely deteriorates the figure of merit (FOM=refractive index sensitivity/full width at half maximum (FWHM)) of these nanostructures, lowering the detection sensitivity. The relatively narrow extinction band of AuNCs (FWHM of about 120 nm) results in a FOM of about 2.7, making them excellent candidates as plasmonic nanotransducers.

Example 13: LSPR Sensitivity and EM Decay Length of AuNCs and AuNRs

In addition to bulk refractive index sensitivity, EM decay length was another important parameter to maximize a LSPR transducer response, which describes the distance-dependent refractive index sensitivity and sensing depth for LSPR sensors. A layer-by-layer (LbL) assembly of polyelectrolytes was employed for probing the distance-dependent LSPR sensitivity and EM decay length of AuNCs and AuNRs. LbL assembly of polyelectrolyte multilayers (PEM), which involves the alternate adsorption of oppositely charged polyelectrolytes, offers an excellent control over the thickness of the dielectric layer down to about 1 nm. The spectra revealed a progressive red-shift in LSPR wavelength and increase in LSPR intensity with the deposition of each bilayer due to the increase in the refractive index of the medium surrounding the plasmonic nanostructures (from air to polymer layer). The cumulative LSPR wavelength shift following the deposition of each polyelectrolyte layer for AuNCs was much higher than AuNRs, especially within the first few nanometers where biomolecule binding events occur, as seen in FIG. 2D.

Owing to the evanescent nature of the EM field at the surface of the plasmonic nanostructures, the LSPR wavelength shift exhibited a characteristic decay with increasing distance from the surface of the nanostructures (i.e. increasing number of layers), given by Eqn. (I):

$$R = m\Delta\eta(1-\exp(-2d/l))$$ Eqn. (I)

where R is LSPR shift, m is the refractive index sensitivity of the nanostructures, $\Delta\eta$ is the change in the refractive index in RIU, d is the adsorbate layer thickness (thickness of the polyelectrolyte layer in this case) and l is the EM decay length. EM decay length of AuNCs was calculated to be about 10.0 nm by fitting the experimental data of LSPR shift using the above exponential equation, which was about 22% smaller compared to that of AuNRs suggesting the higher local sensitivity in the vicinity of AuNCs surface. The high sensitivity of AuNCs was possibly due to the strong electromagnetic fields resulting from the coupling between the external and internal surface plasmon fields in the hollow structures. These results indicate AuNCs to be excellent LSPR biosensors.

Example 14: Molecular Imprinting Procedure

This Example illustrates molecular imprinting the surfaces of AuNCs to create artificial antibodies.

Considering the significantly higher refractive index sensitivity of AuNCs compared to AuNRs, molecular-imprinting on AuNCs using NGAL was performed to produce a highly sensitive plasmonic biosensor for NGAL. NGAL is a biomarker for acute kidney injury. FIG. 3 illustrates the molecular imprinting process on gold nanocages. Poly(vinyl pyrrolidone) (PVP)-capped AuNCs were adsorbed on a poly(2-vinyl pyridine) (P2VP)-modified glass substrate. P-aminothiophenol (p-ATP) and glutaraldehyde (GA) were employed as cross linkers to immobilize biomolecule templates on AuNCs surface by forming reversible imine bonds.

AuNC adsorbed glass substrate was placed in 2 ml of 100 mM NaBH$_4$ aqueous solution for 5 minutes with gentle shaking to remove the PVP coating from AuNCs surface, followed by thorough rinsing with nanopure water. AuNCs adsorbed on the substrate were modified with p-ATP and glutaraldehyde as cross linkers by immersing the substrate in 2 ml of phosphate borate buffer (pH 8.3) containing 4 μL of glutaraldehyde (25%) and 4 μL of pATP (4 mM in ethanol) for 1 minute, followed by rinsing with pH 8.3 buffer. In the next step, template protein (NGAL) was immobilized on nanocages by exposing the substrate to 115 μg/ml of NGAL in a pH 8.3 buffer solution at 4° C. for 2.5 hours, followed by rinsing with a pH 8.3 buffer solution. The NGAL-coated substrate was immersed in 3 ml of phosphate buffered saline (PBS, pH 7.5) containing 15 μL of TMPS and 15 μL of APTMS for 40 minutes. Then the substrate was rinsed with buffer solution and stored in PBS solution at 4° C. overnight. Proteins were released by shaking the substrate in 2 ml of oxalic acid (10 mM) in 2% aqueous sodium dodecyl sulfate (SDS) solution.

Following the immobilization of templates, TMPS and APTMS were copolymerized on template-bound AuNCs. While the Si—C bond and aminopropyl group remain uncleaved, the methoxy groups of APTMS and TMPS undergo rapid hydrolysis to produce ethanol, methanol and trisilanols. The subsequent condensation of the transient silanols yields functional amorphous polymer with amine (—NH3$^+$), hydroxyl (—OH) and propyl (—CH$_2$CH$_2$CH$_3$) functional groups, functioning as artificial antibodies to capture the template molecule and target molecule through the concerted weak interactions, namely electrostatic, hydrogen bonding and hydrophobic interactions. The composition ratio of the siloxane co-polymerization was adjusted to obtain template release and mechanical strength characteristics. The template molecules were removed by breaking the imine bonds with the cross-linker using a mixture of oxalic acid and sodium dodecyl sulfate. The artificial antibodies engineered on the surface of AuNCs selectively bind the target biomolecules, even in the presence of interfering proteins in physiological fluids.

Figure 4A:
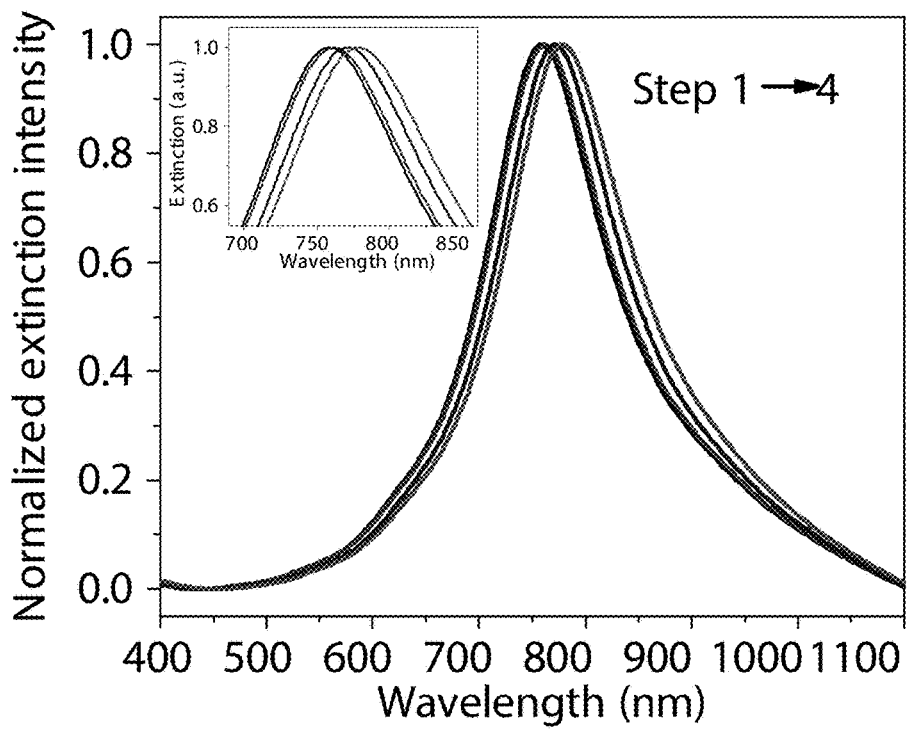
FIG. 4A is a graph summarizing the extinction spectra of Au nanocages at successive stages in a molecular imprinting process, which correspond to AuNC (step 1), AuNC+pATP/GA (step 2), AuNC+pATP/GA+NGAL (step 3), and AuNC+pATP/GA+NGAL+siloxane copolymer (step 4), respectively.
Figure 4B:
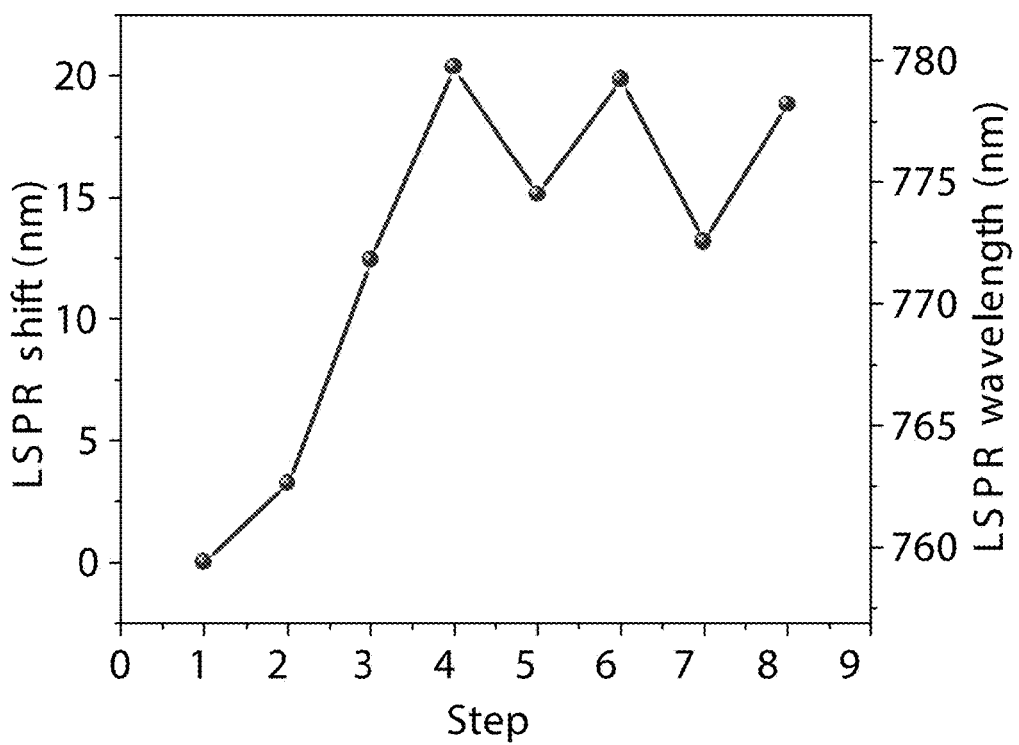
FIG. 4B is a graph summarizing the LSPR wavelengths corresponding to each step in a molecular imprinting process, including two cycles of NGAL protein release and capture.

AuNCs can also function as transducers to monitor each step in molecular imprinting process, including attachment of cross linkers, immobilization of template proteins, polymerization of organo-siloxane monomers, removal of templates, and rebinding of the template protein molecules and target proteins. Extinction spectra of the AuNCs were collected following each step of the imprinting process, as illustrated in FIG. 4. FIG. 4A is an extinction spectra of Au nanocages following each step in molecular imprinting process, which correspond to AuNC (step 1), AuNC+pATP/GA (step 2), AuNC+pATP/GA+NGAL (step 3), and AuNC+pATP/GA+NGAL+siloxane copolymer (step 4), respectively. FIG. 4B shows the LSPR wavelength corresponding to each step in MIP, including two cycles of protein release and capture. The concentration of NGAL for FIGS. 4A and 4B was 230 ng/ml.

The spectra revealed a progressive red-shift in LSPR wavelength with the deposition of each layer (i.e., from steps 604 to 608 as show in FIG. 6) due to the increase in the refractive index (from buffer to the mixture of polymer layer and buffer). FIG. 4B also shows two cycles of release and capture of target proteins, resulting in blue and red LSPR wavelength shift respectively, demonstrating the reusability of molecularly imprinted AuNCs.

Example 15: NGAL Detection and Interfering Proteins Test

After removing template proteins, the molecularly imprinted AuNCs on glass substrates were immersed in 1 ml of different concentrations of NGAL in pH 8.3 buffer solution, followed by gently shaking for 30 minutes and then incubation at 4° C. for 3.5 hours. The same procedure was used to test interfering proteins, including myoglobin from human heart (10 μg/ml), hemopexin from human plasma (10 μg/ml), antitrypsin from human plasma (10 μg/ml), acid glycoprotein from human plasma (10 μg/ml), albumin from human serum (10 μg/ml), hemoglobin (10 μg/ml), FABP1 (1 μg/ml) and FABP3 (1 μg/ml). Extinction spectra were collected from at least three samples for different concentrations of NGAL and interfering proteins to obtain the average LSPR wavelength shift.

Figure 5A:
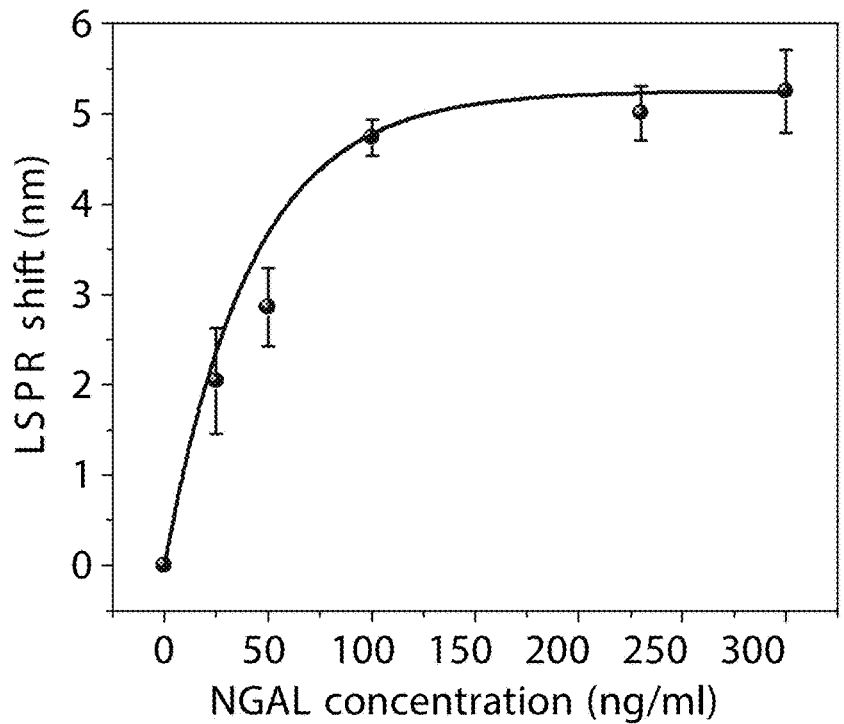
FIG. 5A is a graph summarizing the LSPR shift in nm as a function of NGAL concentration for NGAL imprinted gold nanocages.

FIG. 5A shows the LSPR shift of interfering proteins (>10 μg/ml) compared with NGAL (0.3 μg/ml). This demonstrated the shift in the LSPR wavelength of AuNCs upon exposure to different concentrations of NGAL in artificial urine, which encompasses the physiological and pathological concentration range. Other human urinary proteins with lipocalin-like domains such as FABP1, FABP3 or orosomucoid; and myoglobin or hemopexin (1-10 μg/ml); and hemoglobin or serum albumin (up to 500 μg/ml) interfered less than 20% with the LSPR signal of NGAL. A monotonic increase in the LSPR shift was observed with increasing concentrations of NGAL in artificial urine. Patients with urine NGAL concentration of 125 ng/ml or less do not typically progress to acute kidney injury (AKI), while patients with urine NGAL concentration of 350 ng/ml progress to AKI. The LSPR shift was about 5 nm for 125 ng/ml (5 nM) of NGAL, which is the critical concentration to differentiate patient progression to AKI. NGAL was detected to 25 ng/ml (LSPR shift of about 2 nm), which is much lower than the concentration range of NGAL in urine of patients with AKI.

Figure 5B:
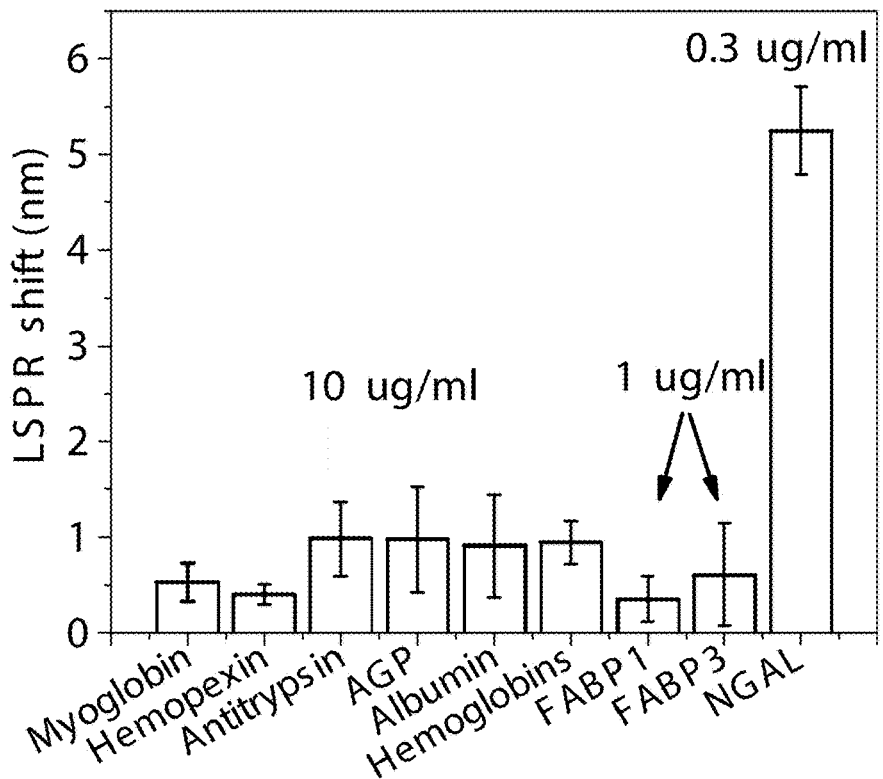
FIG. 5B is a bar graph summarizing the LSPR shift of various interfering proteins (>10 μg/ml) compared with NGAL (0.3 μg/ml).

To test the selectivity of artificial antibodies, the NGAL-imprinted AuNCs were challenged with high concentrations of other urinary proteins as potentially interfering molecules, including 10 μg/ml of myoglobin (MW=17.7 kDa), hemopexin (MW=57 kDa), α1-antitrypsin (MW=52 kDa), α1-acid glycoprotein (MW=40.8 kDa), albumin (MW=66.5 kDa), and hemoglobins (MW=64.5 kDa), and 1 μg/ml of recombinant human fatty acid-binding protein 1 (FABP1) (MW=14.2 kDa), and recombinant human fatty acid binding protein-3 (FABP3) (MW=14.8 kDa). FIG. 5B illustrates an LSPR shift of interfering proteins (>10 μg/ml) compared with NGAL (0.3 μg/ml). The LSPR shift from all interfering proteins at significantly higher concentration (1-2 orders magnitude) was less than 1 nm, which was much smaller compared to about 5 nm for NGAL.

Example 16: NGAL in Different pH Value and Specific Gravity of Artificial Urine Test The molecularly imprinted AuNCs coated substrates were immersed in 1 ml of 230 ng/ml NGAL in artificial urine with different pH (4.5, 5.5, 6.5, 7.5 and 8.5) and specific gravity (1.005, 1.010, 1.020, 1.030), followed by gently shaking for 30 minutes and incubation at 4° C. for 3.5 hours. Extinction spectra were collected from at least three samples to obtain average LSPR wavelength shift.

Figure 5C:
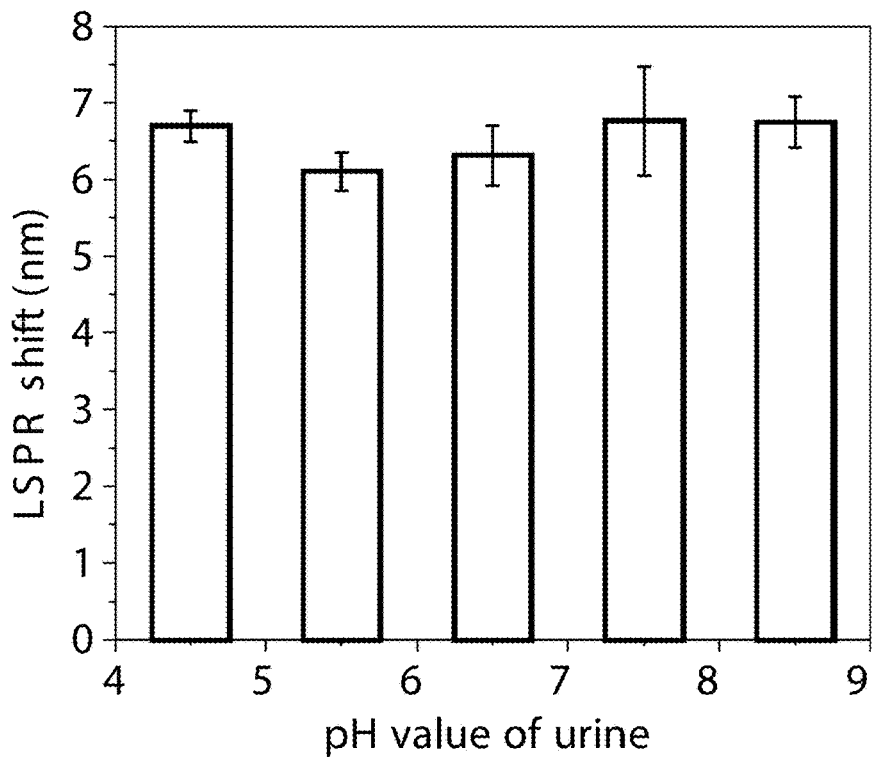
FIG. 5C is a graph summarizing the LSPR shift of 230 ng/ml of NGAL in different PH values of artificial urine.
Figure 5D:
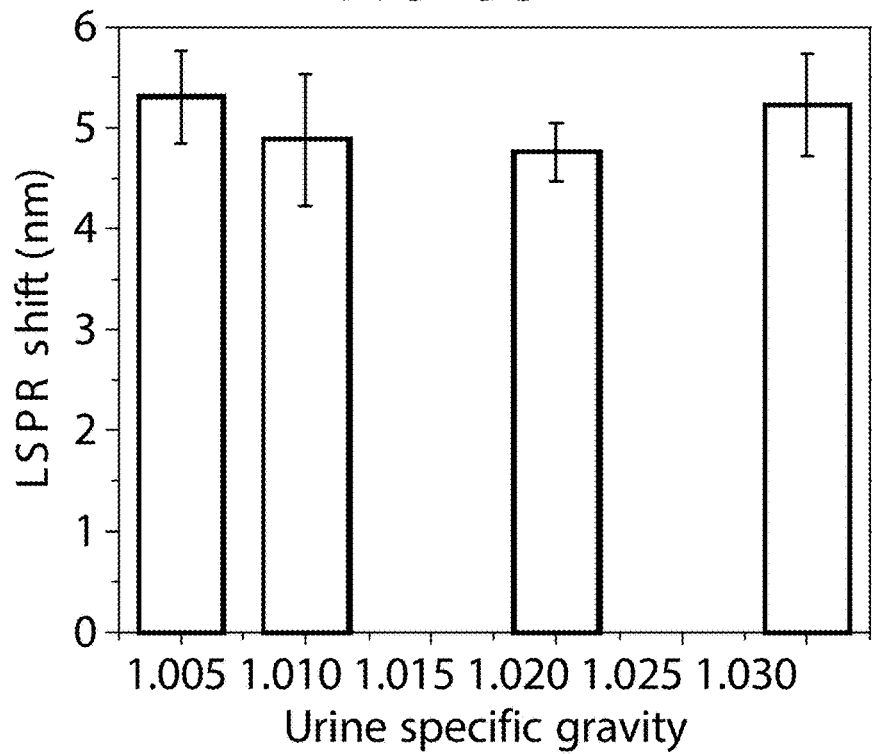
FIG. 5D is a graph summarizing the LSPR shift of 230 ng/ml of NGAL in different specific gravities of artificial urine.

The pH value of human urine can range from 4.5 to 8.5 depending on diet or other pathological conditions of subjects. FIG. 5C shows an LSPR shift of 230 ng/ml of NGAL in different PH values of artificial urine. As illustrated in FIG. 5C, an LSPR shift of molecularly imprinted AuNC upon exposure to artificial urine at different pH (4.5-8.5) spiked with 230 ng/ml of NGAL exhibited only a small variation indicating the remarkable pH stability of artificial antibodies. The plasmonic sensor response to 230 ng/ml of NGAL was also tested in urine of different specific gravities (1.005 to 1.030 g/ml). FIG. 5D illustrates an LSPR shift of 230 ng/ml of NGAL in different specific gravities of artificial urine. The LSPR shift exhibited a remarkable stability over the range of specific gravities tested, suggesting the excellent stability of the artificial antibodies. These results clearly suggest the robustness and efficiency of NGAL imprinted AuNCs as plasmonic nanotransducers with built-in recognition elements for the detection of target biomarkers under complex physiological conditions.

Example 17: Plasmonic Nanorattles

In this Example, gold nano-octahedra, employed as cores, were used to prepare plasmonic nanorattles (FIG. 15).

Gold nano-octahedra, employed as cores, were synthesized using a seed-mediated method with cetyltrimethylammonium bromide (CTAB) as the stabilizing agent. Au octahedron particles were synthesized following a seed-mediated growth process. The seed solution was prepared by mixing 7.5 mL aqueous CTAB solution (0.1M) and 2.5 mL of $HAuC_{14}$ (1 mM) in a 20 mL scintillation vial, followed by the rapid addition of 0.6 mL of ice-cold $NaBH_4$ (10 mM) under vigorous stirring to yield a brown colored seed solution. The seed solution was diluted 100 times for the growth of Au octahedrons after 3 h of aging. Growth solution was prepared by adding 7.7 mL of $HAuC_{14}$ (0.05 mM) and 0.6 mL of ascorbic acid (0.1M) to 1.6 mL of CTAB (0.1M) and under vigorous stirring. To the growth solution 120 µL of the diluted seed was added and the reaction mixture was left undisturbed for about 12 h after vigorous mixing for 30 sec.

Figure 16A:
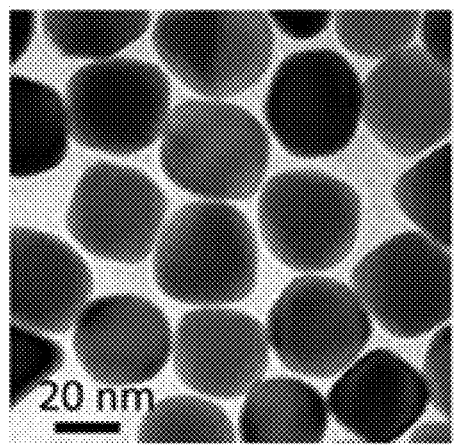
FIG. 16A is a TEM image depicting gold nano-octahedra core.

Au nano-octahedra were found to be monodisperse with a body length of 36.5±3.2 nm (n>100) as measured from the transmission electron microscope (TEM) images (FIG. 16A).

Figure 16B:
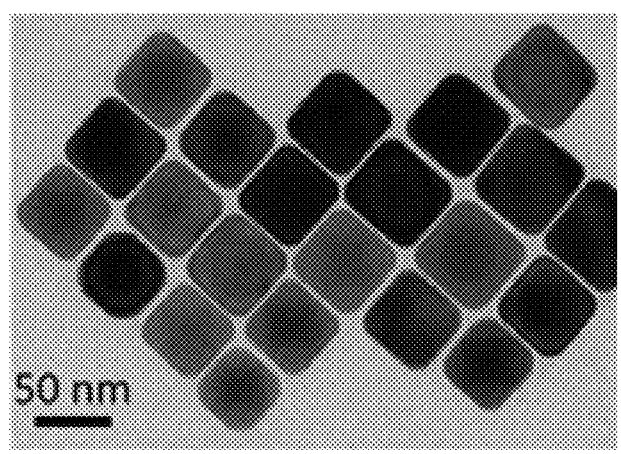
FIG. 16B is a TEM image depicting gold nanocubes with silver shells.
Figure 16C:
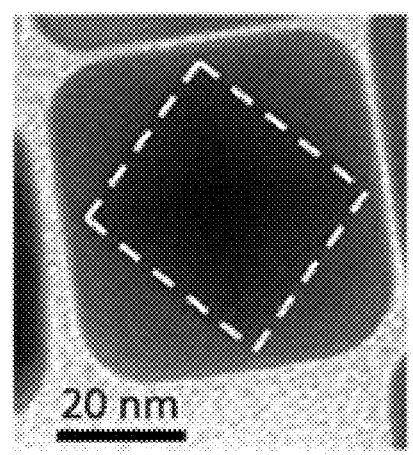
FIG. 16C is a TEM image depicting a gold nanocubes with silver shells with a dotted line outlining the gold core.

For the synthesis plasmonic nanorattles, Au nano-octahedra where coated with a thin layer of silver to form "Au@Ag" nanoparticles. In particular, 0.5 mL of $AgNO_3$ (10 mM) and 2 ml of ascorbic acid (0.1M) were added to 5 mL of a prepared Au octahedron seed solution under stirring (as illustrated in FIG. 15). The solution was kept in an oil bath at 60° C. for 20 h to complete the growth, resulting in a yellow color solution. A thin silver shell was formed on the nano-octahedra by introducing the prepared Au nano-octahedra into a silver growth solution comprised of silver precursor ($AgNO_3$), ascorbic acid as the reducing agent and CTAB as the stabilizer. Epitaxial growth of the silver shell on the Au cores resulted in the formation of core-shell nanocubes. The synthesized Au@Ag nanocubes were monodisperse with an edge length of 44.5±2.5 nm (n>100) as determined from the TEM images (FIG. 16B). After the silver shell formation, the nano-octahedra exhibited sharp edges of as evidenced by the TEM images. Since, a gold nano-octahedra solution was used for the growth of silver shell, possibly the unreacted Au ions in presence of $Ag^+$ ions led to the formation of sharp corners (FIG. 16C).

Galvanic replacement reaction was carried out in order to create the nanorattle structure where the gold octahedron core remains embedded within the porous Au shell. In particular, 6 mL of the Au@Ag nanoparticles solution were centrifuged at 10,000 rpm for 10 min and suspended in 6 mL of PAH solution (6 mg/mL in 6 mM NaCl), followed by the sonication for 1 h. The resultant solution was centrifuged again at 10,000 rpm for 10 min and dispersed in 90 mM PVP solution used for galvanic replacement reaction. $HAuC_{14}$ aqueous solution (0.5 mM) was injected to the above mildly boiled Au@Ag solution at a rate of 0.25 mL/min under vigorous magnetic stirring until a blue colored solution appeared. The solution was allowed to stand for about 2 h to precipitate AgCl byproduct. The solution was then centrifuged at 7,000 rpm for 10 min and dispersed in nanopure water for further use. Prior to the replacement reaction, the capping agent CTAB was replaced with poly(allylamine hydrochloride) (PAH) and the reaction was carried out in presence of poly(vinyl pyrollidone) (PVP).

Generally, the galvanic replacement reaction for the formation of an Ag nanocube is conducted in the presence of PVP as a stabilizer. However, aggregation of the Au@Ag nanoparticles was observed while dispersing the particles in PVP solution, as evidenced by the change in the shape of the LSPR band of Au@Ag nanoparticle solution and large aggregates of Au@Ag nanoparticles observed in the SEM images. To overcome this issue, the capping agent, CTAB, was exchanged with PAH and then the galvanic replacement reaction was performed.

Figure 16D:
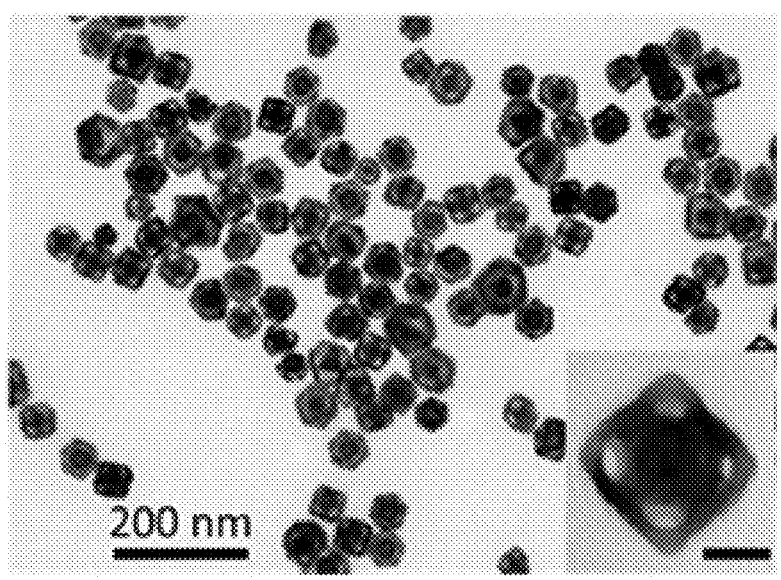
FIG. 16D is a TEM image depicting a plurality of plasmonic nanorattles (insert shows a single plasmonic nanorattle).

TEM images of Au nanorattles showed the presence of porous cubic Au shell surrounding the intact octahedron Au core, where the vertices of the octahedron touched the faces of the cubic shell structure. From the TEM images, the size of the nanorattles was determined to be 54.6±4.5 nm (n>100) and the wall thickness of the shell was estimated to be ~7 nm (FIG. 16D).

Figure 17:
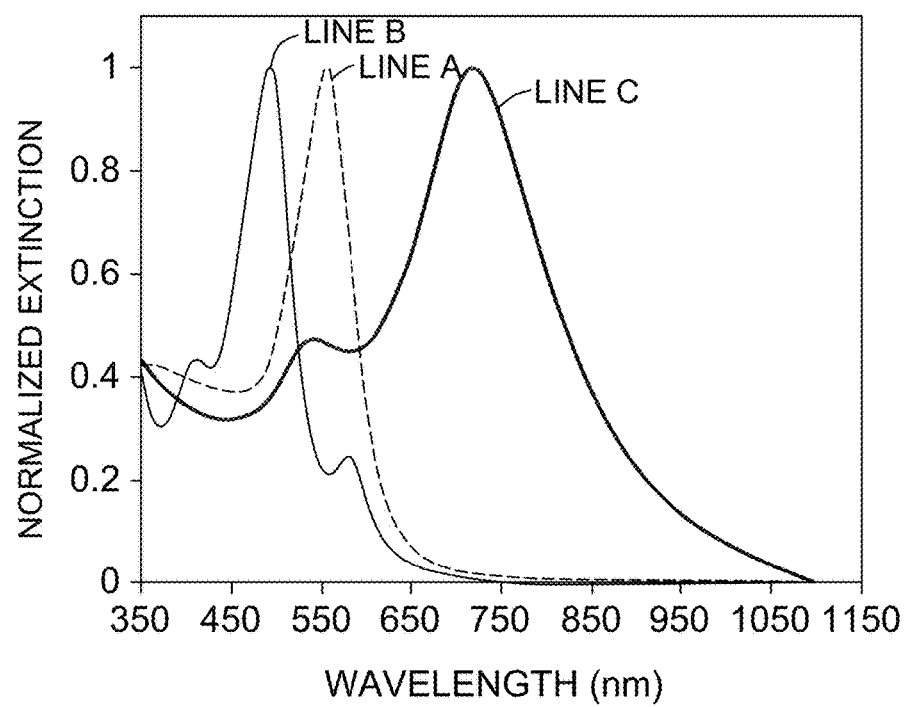
FIG. 17 is a graph illustrating the extinction spectra of gold nano-octahedra core, gold nanocubes with silver shells and plasmonic nanorattles as analyzed by LSPR.

As depicted in FIG. 17, Au nano-octahedra exhibited a localized surface plasmon resonance (LSPR) peak at around 555 nm (FIG. 17, line A). The extinction spectrum of Au@Ag nanoparticles revealed three distinct peaks at 412 nm, 486 nm and 580 nm (FIG. 17, line B). The peaks at 412 and 486 nm are consistent with those observed in case of Ag nanocubes, while the 580 nm peak is ascribed to the inner Au core particle and coupling between gold and silver at the interface. The Galvanic replacement reaction resulted in the disappearance of LSPR peaks corresponding to the Ag shell with a concomitant rise of a new higher wavelength band that exhibited progressive red-shift with increase in the amount of Au precursor added to the reaction. The extinction spectrum of the Au nanorattles displayed a major peak at 710 nm and a minor peak corresponding to the Au octahedron core at 555 nm (FIG. 17, line C). A photograph of Au core, Au@Ag and Au nanorattles solutions under ambient light demonstrated the distinct extinction characteristics of the nanostructures (FIG. 16D).

These Examples demonstrate the preparation and use of plasmonic nanotransducers having hollow nanostructure cores and artificial antibodies. The preparation of the plasmonic nanotransducers can be monitored for polymer thickness, template molecule binding and removal, and target molecule binding (capture) and release using LSPR and SERS. The plasmonic nanotransducers provide a label-free method for detecting any target molecule of interest in biological samples.

All of the compositions and/or methods disclosed and claimed herein may be made and/or executed without undue experimentation in light of the present disclosure. While the compositions and methods of this disclosure have been described in terms of the embodiments included herein, it will be apparent to those of ordinary skill in the art that variations may be applied to the compositions and/or methods and in the steps or in the sequence of steps of the method described herein without departing from the concept, spirit, and scope of the disclosure. All such similar substitutes and modifications apparent to those skilled in the art are deemed to be within the scope and concept of the disclosure as defined by the appended claims.

What is claimed is:

1. A plasmonic nanotransducer comprising:
a hollow nanostructure core, wherein the hollow nanostructure core is selected from the group consisting of a nanocage, a nanorattle, a nanoshell, and a nanomatryoshka; and
functional monomers polymerized to the hollow nanostructure core, wherein the polymerized functional monomers comprise at least one recognition cavity that is substantially complementary to a target molecule.

2. The plasmonic nanotransducer of claim 1, wherein the functional monomers comprise a silane, acrylamide, and combinations thereof.

3. The plasmonic nanotransducer of claim 2, wherein the silane is selected from the group consisting of an organic silane monomer, 3-aminopropyltrimethoxysilane, propyltrimethoxysilane, benzyltriethoxysilane, benzyldimethylchlorosilane, acetamidopropyltrimethoxysilane, and combinations thereof.

4. The plasmonic nanotransducer of claim 3, wherein the organic silane monomer is functionalized with a macromolecule.

5. The plasmonic nanotransducer of claim 4, wherein the macromolecule is adsorbed to the functional monomers.

6. The plasmonic nanotransducer of claim 5 wherein the macromolecule is selected from the group consisting of polyethylene glycol and albumin.

7. A method of preparing a plasmonic nanotransducer comprising a hollow nanostructure core and functional monomers adhered to the hollow nanostructure core, the method comprising
synthesizing a hollow nanostructure core, wherein the hollow nanostructure core is selected from the group consisting of a nanocage, a nanorattle, a nanoshell, and a nanomatryoshka;
immobilizing at least one template molecule on the surface of the hollow nanostructure core to form a template molecule-nanostructure core structure;
polymerizing functional monomers onto the template molecule-nanostructure core structure; and
removing the template molecule to form at least one recognition cavity in the polymerized functional monomers upon removal of the template molecule, wherein the at least one recognition cavity is substantially complementary to a target molecule.

8. The method of claim 7, wherein the functional monomers comprise a silane, acrylamide, and combinations thereof.

9. The method of claim 8, wherein the silane is selected from the group consisting of an organic silane monomer, 3-aminopropyltrimethoxysilane, propyltrimethoxysilane, benzyltriethoxysilane, benzyldimethylchlorosilane, acetamidopropyltrimethoxysilane, and combinations thereof.

10. The method of claim 9, wherein the organic silane monomer is functionalized with a macromolecule selected from the group consisting of polyethylene glycol and albumin.

11. The method of claim 7, wherein the removing step comprises exposing the template molecule-nanostructure core structure to a reagent selected from the group consisting of oxalic acid, sodium dodecyl sulfate (SDS), and combinations thereof.

12. The method of claim 7, further comprising adsorbing to the functional monomer a molecule selected from the group consisting of polyethylene glycol and albumin prior to removing the template molecule.

13. A label-free method for detecting a target molecule in a biological sample, the method comprising:
obtaining a biological sample from a subject;
contacting the biological sample with a plasmonic nanotransducer, wherein the plasmonic nanotransducer comprises:
a hollow nanostructure core, wherein the hollow nanostructure core is selected from the group consisting of a nanocage, a nanorattle, a nanoshell, and a nanomatryoshka; and
functional monomers polymerized to the hollow nanostructure core, wherein the polymerized functional monomers comprise at least one recognition cavity that is substantially complementary to a target molecule;
wherein the target molecule in the biological sample forms a complex with the plasmonic nanotransducer; and
detecting the complex.

14. The method of claim 13, wherein the complex is detected using a method selected from the group consisting of local surface plasmon resonance and surface enhanced Raman scattering.

15. The method of claim 13, wherein the hollow nanostructure core is selected from the group consisting of a hollow gold nanostructure core, a hollow silver nanostructure core, a hollow copper nanostructure core, and combinations thereof.

16. The method of claim 13, wherein the biological sample comprises a liquid biological sample.

17. The method of claim 16, wherein the liquid biological sample is selected from the group consisting of whole blood, plasma, serum, urine, saliva, cerebrospinal fluid, and sweat.

18. The method of claim 13, wherein the target molecule is selected from the group consisting of a cell, a protein, a peptide, a nucleic acid, and combinations thereof.

19. The method of claim 13, further comprising adsorbing the plasmonic nanotransducer to a substrate prior to contacting the biological sample with the plasmonic nanotransducer.

20. The method of claim 19, wherein the substrate is selected from the group consisting of a glass substrate, a paper substrate, and a fibrous mat.

* * * * *